(12) United States Patent
Olsen et al.

(10) Patent No.: US 6,548,063 B1
(45) Date of Patent: Apr. 15, 2003

(54) SYNFERON

(75) Inventors: Henrik S. Olsen, Gaithersburg, MD (US); Reiner L. Gentz, Rockville, MD (US); Steven M. Ruben, Olney, MD (US)

(73) Assignee: Human Genome Sciences, Inc., Rockville, MD (US)

( * ) Notice: Subject to any disclaimer, the term of this patent is extended or adjusted under 35 U.S.C. 154(b) by 0 days.

(21) Appl. No.: 09/604,073

(22) Filed: Jun. 27, 2000

Related U.S. Application Data

(62) Division of application No. 09/205,264, filed on Dec. 2, 1998, now Pat. No. 6,114,145.
(60) Provisional application No. 60/067,746, filed on Dec. 5, 1997.

(51) Int. Cl.[7] .................. A61K 39/395; A61K 38/21; C07K 17/00; C07K 16/00; C12P 21/06
(52) U.S. Cl. .................. 424/158.1; 530/350; 530/351; 530/388.1; 530/389.1; 429/85.4; 435/325
(58) Field of Search .................. 530/388.1, 389.1, 530/350, 351; 424/158.1, 85.4; 435/325

(56) References Cited

U.S. PATENT DOCUMENTS 4,695,623 A * 9/1987 Stabinsky
4,975,278 A * 12/1990 Senter et al.

FOREIGN PATENT DOCUMENTS

| EP | 490 233 A1 | 6/1992 |
| WO | WO96/40934 A1 | 12/1996 |
| WO | WO99/29862 | 6/1999 |

OTHER PUBLICATIONS

Genbank Accession No.: CAA02581.
Genbank Accession No.: CAA01011.
Genbank Accession No.:CAA00963.
Genbank Accession No.:CAA00297.
Genbank Accession No.:AAA52724.
Genbank Accession No.:AAA36042.
Genbank Accession No.:CAA24970.
Genbank Accession No.:CAA01251.
Genbank Accession No.:AAA70091.
Genbank Accession No.:CAB41665.
Genbank Accession No.:CAA02580.
Genbank Accession No.:CAA01007.
Genbank Accession No.:AAA59181.
Genbank Accession No.:CAA01220.
Genbank Accession No.:CAA00295.
Genbank Accession No.:CAA02075.
Genbank Accession No.:AAC64915.
Genbank Accession No.:CAA72532.
Austruy et al., Cancer Gene Ther., vol. 5(4):247–56 (1998) (abstract only).

Capon et al., Mol. Cell Biol., vol. 5(4):768–79 (1985) (abstract only).
Gren et al., J. Interferon Res., vol. 4(4):609–17 (1984) (abstract only).
Zhao et al., Anal. Biochem., vol. 178(2):342–7 (1989) (abstract only).
Henco et al., J. Mol. Biol., vol. 185(2)227–60 (1985) (abstract only).
Hauptmann et al., Genbank Accession No.: CAA02581.
Hauptmann et al., Genbank Accession No.: CAA01011.
Hauptmann et al., Genbank Accession No.:CAA00963.
Hauptmann et al., Genbank Accession No.:CAA00297.
Capon et al., Genbank Accession No.:AAA52724.
Gren et al., Genbank Accession No.:AAA36042.
Gren et al., Genbank Accession No.:CAA24970.
Atherton et al., Genbank Accession No.:CAA01251.
Zeng et al., Genbank Accession No.:AAA70091.
Zhao et al., Genbank Accession No.:CAB41665.
Hauptmann et al., Genbank Accession No.:CAA02580.
Weissmann et al., Genbank Accession No.:CAA01007.
Oliver et al., Genbank Accession No.:AAA59181.
Kingsman et al., Genbank Accession No.:CAA01220.
Hauptmann et al., Genbank Accession No.:CAA00295.
Adolf et al., Genbank Accession No.:CAA02075.
Fiorini et al., Genbank Accession No.:AAC64915.
Austruy et al., Genbank Accession No.:CAA72532.
Austury et al., *A Defective Retrovial Vector Encoding Human Interferon–Alpha2 Can Transduce Human Leukemic Cell Lines*, Cancer Gene Ther., vol. 5(4):247–56 (1998).
Capon et al., *Two Distinct Families Of Human And Bovine Interferon–Alpha Genes Are Coordinately Expressed And Encode Functional Polypeptides*, Mol. Cell Biol., vol. 5(4):768–79 (1985).
Gren et al., *Novel Human Leukocyte Interferon Subtype And Structural Comparison Of Alpha Interferon Genes*, J. Interferon Res., vol. 4(4):609–17 (1984).
Zhao et al.,*Construction And Phsphorylation Of A Fusion Protein Hu–IFN–Alpha A/Gamma*, Anal. Biochem., vol. 178(2):342–7 (1989).
Henco et al., *Structural Relationship Of Human Interferon Alpha Genes And Pseudogenes*, J. Mol. Biol., vol. 185(2)227–60 (1985).

* cited by examiner

Primary Examiner—Yvonne Eyler
Assistant Examiner—Janet L. Andres
(74) Attorney, Agent, or Firm—Human Genome Sciences, Inc.

(57) ABSTRACT

The present invention relates to a novel Synferon protein which is a member of the interferon family. In particular, isolated nucleic acid molecules are provided encoding a synthetic interferon polypeptide, called "Synferon". Synferon polypeptides are also provided as are vectors, host cells and recombinant methods for producing the same. The invention further relates to screening methods for identifying agonists and antagonists of Synferon activity. Also provided are therapeutic methods for treating immune system-related disorders.

69 Claims, 3 Drawing Sheets

FIGURE 1

```
  1 ATG TGC GAC CTG CCG GAA ACC CAC TCT GAC TCT CGT AAC ACC GTT CTG CAC  60
    Met Cys Asp Leu Pro Glu Thr His Ser Asp Ser Arg Asn Thr Val Leu His
    M   C   D   L   P   E   T   H   S   D   S   R   N   T   V   L   H

61 CAG ATG CGT CGT ATC ATC TCT CCG TCT CTG TGC CTG AAA CAC GAC TTC CCG 120
    Gln Met Arg Arg Ile Ile Ser Pro Ser Leu Cys Leu Lys His Asp Phe Pro
    Q   M   R   R   I   I   S   P   S   L   C   L   K   H   D   F   P

121 CAG GAA GAA GTT AAA GTT GGT TCT GGT TCT AAA ATC CAG AAA CTG GTT CTG CAC AAA 180
    Gln Glu Glu Val Lys Val Gly Ser Gly Ser Lys Ile Gln Lys Leu Val Leu His Lys
    Q   E   E   V   K   V   G   S   G   S   K   I   Q   K   A   L   V   H   K

181 GTT CTG CAG CAG ATC ATC GTT ACC TTC CTG ACC AAC GCT CAC ACC ACC ACC GTT CTG ACC GGT 240
    Val Leu Gln Gln Ile Ile Val Thr Phe Leu Thr Asn Ala His Thr Thr Thr Val Leu Thr Gly
    V   L   Q   Q   I   I   V   T   F   L   T   N   A   H   T   T   T   V   L   T   G

241 CTG GAA AAA CTG TTC TTC GAA ACC TAC TTC CAG CAC TGG CAC CGT TCT GTT GGT TGG CTG GAA GTT CTG GAA GTT CCG GAA TGC CTG CTG 300
    Leu Glu Lys Leu Phe Phe Glu Thr Tyr Phe Gln His Trp Gln His Arg Ser Val Gly Trp Leu Glu Val Leu Glu Val Pro Glu Cys Leu Leu
    L   E   K   L   F   F   E   T   Y   F   Q   H   W   Q   H   R   S   V   G   W   L   E   V   L   E   V   P   C   L   L

301 AAC GAA CTG GGT GTT GAA GGT CTG TCT TAC CTG CTG TCT CAG GCT ATG ACC ACC ACC CCG AAC GCT GTT AAA TCT 360
    Asn Glu Leu Gly Val Glu Gly Leu Ser Tyr Leu Leu Ser Gln Ala Met Thr Thr Thr Pro Asn Ala Val Lys Ser
    N   E   L   G   V   E   G   L   S   Y   L   L   S   Q   A   M   T   T   T   P   N   A   V   K   S

361 TAC TTC CAG TTC CAG GGT ATC ATC TCT CTG CTG TAC CTG GAA AAA CTG AAA GAA GAA TCT TGC ACC TGG GAA 420
    Tyr Phe Gln Phe Gln Gly Ile Ile Ser Leu Leu Tyr Leu Glu Lys Leu Lys Glu Glu Ser Cys Thr Trp Glu
    Y   F   Q   F   Q   G   I   I   S   L   L   Y   L   E   K   L   K   E   E   S   C   T   W   E

421 GTT GGT GCT GAA ATC ATG ATC CGT AGC TTC TTC TCT AAC AGC CTG CAG GTT CGT CTG ATC 480
    Val Gly Ala Glu Ile Met Ile Arg Ser Phe Phe Ser Asn Ser Leu Gln Val Arg Leu Ile
    V   G   A   E   I   M   I   R   S   F   F   S   N   S   L   Q   V   R   L   I

481 GCT 483
    Ala
    A
```

FIGURE 2

```
                30           40           50           60           70           80
       CDLPQNHGLLSRNTLVLLHQMRRISPFLCLKDRRDFRFPQEMVKGSQLQKAHVMSVLHEM
       ::::  :::   ::::::::::::::  ::  ::::    ::::    ::::  :::  
       CDLPETHSLDSRNTTVLLHQMRRISPSLCLKDRHDFGFPQEEVKGSKIQKAHTTVLHKV
                10           20           30           40           50           60

90          100          110          120          130          140
       LQQIFSLFHTERSSAAWNMTLLDQLHTGLHQQLQHLETCLLQVVGEGESAGAISSPALTL
       :::  :  :: :      ::: ::  :   :::  :   ::  :::              
       LQQIVTLFNTR--SVGWNETGLEKLFTEFYQHWEVLEPCLLNELGVEGLSQAMTTPN-AV
               70           80           90          100          110

150          160          170          180
       RRYFQGIRVYLKEKKYSDCAWEVVRMEIMKSLFLSTNMQERL
         :::::  :: :::::   :  :::   ::::  :::    
       KSYFQGISLYLEKKEESLCTWE--VGAEIMRSFFFSSNLQVRL
              120          130          140          150
```

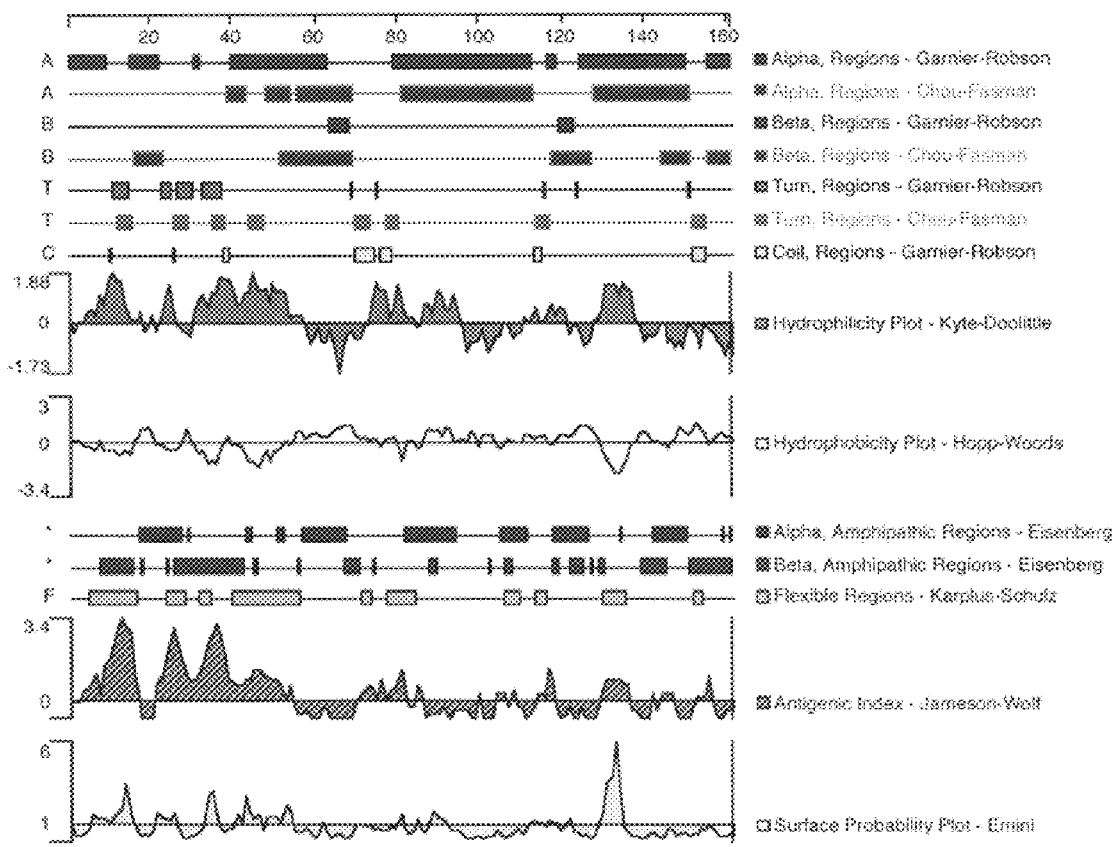

SYNFERON

This application is a Divisional of U.S. application Ser. No. 09/205,264, filed Dec. 2, 1998, now issued as U.S. Pat. No. 6,114,145, which claims priority to U.S. Provisional Application Serial No. 60/067,746, filed Dec. 5, 1997, and is hereby incorporated in its entirety.

FIELD OF THE INVENTION

The present invention relates to a novel synthetic gene encoding a polypeptide which is a member of the interferon family. More specifically, isolated nucleic acid molecules are provided encoding a synthetic polypeptide named "Synferon". Synferon polypeptides are also provided, as are vectors, host cells and recombinant methods for producing the same. Also provided are therapeutic methods for treating disorders of the immune system.

BACKGROUND OF THE INVENTION

Interferons (IFNs) are a well known family of cytokines secreted by a large variety of eukaryotic cells upon exposure to various stimuli. The interferons have been classified by their chemical and biological characteristics into four groups: IFN-alpha (leukocytes), IFN-beta (fibroblasts), IFN-gamma (lymphocytes), and IFN-omega (leukocytes). IFN-alpha and beta are known as Type I interferons; IFN-gamma is known as a Type-II or immune interferon. A single functional gene in the human genome codes for interferon omega (IFN-omega), a monomeric glycoprotein distantly related in structure to IFN-alpha and IFN-beta, but unrelated to IFN-gamma. IFN-omega is secreted by virus-infected leukocytes as a major component of human leukocyte interferon. The IFNs exhibit anti-viral, immunoregulatory, and antiproliferative activity. The clinical potential of interferons has been recognized, and will be summarized below.

Anti-viral: IFNs have been used clinically for anti-viral therapy, for example, in the treatment of AIDS (Lane, *Semin. Oncol.* 18:46–52 (October 1991)), viral hepatitis including chronic hepatitis B, hepatitis C (Woo, M. H. and Brunakis, T. G., *Ann. Pannacother*, 31:330–337 (March 1997); Gibas, A. L., *Gastroenterologist*, 1:129–142 (June 1993)), hepatitis D, papilloma viruses (Levine, L. A. et al., *Urology* 47:553–557 (April 1996)), herpes (Ho, M., *Annu. Rev. Med.* 38:51–59 (1987)), viral encephalitis (Wintergerst et al., *Infection*, 20:207–212 (July 1992)), and in the prophylaxis of rhinitis and respiratory infections (Ho, M., *Annu. Rev. Med.* 38:51–59 (1987)).

Anti-parasitic: IFNs have been suggested for anti-parasite therapy, for example, IFN-gamma for treating *Cryptosporidium parvum* infection (Rehg, J. E., *J. Infect. Des.* 174:229–232 (July 1996)).

Anti-bacterial: IFNs have been used clinicaly for anti-bacterial therapy. For example, IFN-gamma has been used in the treatment of multidrug-resistant pulmonary tuberculosis (Condos, R. et al., *Lancet* 349:1513–1515 (1997)).

Anti-cancer: Interferon therapy has been used in the treatement of numerous cancers (e.g., hairy cell leukemia (Hofmann et al., *Cancer Treat. Rev.* 12 (*Suppl. B*):33–37 (December 1985)), acute myeloid leukemia (Stone, R. M. et al. *Am. J. Clin. Oncol.* 16:159–163 (April 1993)), osteosarcoma (Strander, H. et al., Acta Oncol. 34:877–880 (1995)), basal cell carcinoma (Dogan, B. et al., *Cancer Lett.* 91:215–219 (May 1995)), glioma (Fetell, M. R. et al., *Cancer* 65: 78–83 (January 1990)), renal cell carcinoma (Aso, Y. et al. *Prog. Clin. Biol. Res.* 303:653–659 (1989)), multiple myeloma (Peest, D. et al., *Br. J. Haematol.* 94:425–432 (September 1996)), melanoma (Ikic, D. et al., *Int. J. Dermatol.* 34:872–874 (December 1995)), and Hodgkin's disease (Rybak, M. E. et al., *J. Biol. Response Mod.* 9:1–4 (February 1990)). Synergistic treatment of advanced cancer with a combination of alpha interferon and temozolomide has also been reported (Patent publication WO 9712630 to Dugan, M. H.).

Immunotherapy: IFNs have been used clinically for immunotherapy or more particularly, (1) for example, to prevent graft vs. host rejection, or to curtail the progresion of autoimmune diseases, such as arthritis, multiple sclerosis, (2) or diabetes (3). IFN-beta is approved of sale in the United States for the treatment (i.e., as an immunosuppressant) of multiple sclerosis. Recently it has been reported that patients with multiple sclerosis have diminished production of type I interferons and interleukin-2 (Wandinger, K. P. et al., *J. Neurol. Sci.* 149: 87–93 (1997)). In addition, immunotherapy with recombinant IFN-alpha (in combination with recombinant human IL-2) has been used successfully in lymphoma patients following autologous bone marrow or blood stem cell transplantation, that may intensify remission following translation (Nagler, A. et al., *Blood* 89: 3951–3959 (June 1997)).

Anti-allergy: The administration of IFN-gamma has been used in the treatment of allergies in mammals (See, Patent Publication WO 8701288 to Parkin, J. M. and Pinching, A. J.). It has also recently been demonstrated that there is a reduced production of IL-12 and IL-12-dependent IFN-gamma release in patients with allergic asthma (van der Pouw Kraan, T. C. et al., *J. Immunol.* 158:5560–5565 (1997)). Thus, IFN may be useful in the treatment of allergy by inhibiting the humoral response.

Vaccine adjuvantation: Interferons may be used as an adjuvant or coadjuvant to enhance or simulate the immune response in cases of prophylactic or therapeutic vaccination (Heath, A. W. and Playfair, J. H. L., *Vaccine* 10:427–434 (1992)).

Clearly, there exists a need in the art for the discovery of novel interferon proteins for numerous applications, in e.g., immunotherapy, as well as anti-viral, anti-parasitic, anti-bacterial, or anti-cancer therapies, or any medical condition or situation where increased interferon activity is desired.

SUMMARY OF THE INVENTION

The present invention provides isolated nucleic acid molecules comprising a polynucleotide encoding at least a portion of the Synferon polypeptide having the complete amino acid sequence shown in SEQ ID NO:2 or the complete amino acid sequence encoded by the DNA clone ("HKIXK74") deposited as plasmid DNA as ATCC Deposit Number 209522 on Dec. 9, 1997. The American Type Culture Collection is located at 10801 University Boulevard, Manassas, Va. 20110-2209. The designation for HKIXK74 given to the ATCC is DNA Plasmid PF404. The nucleotide sequence which is shown in FIG. 1 (SEQ ID NO:1), contains an open reading frame encoding a complete polypeptide of 161 amino acid residues, including an initiation codon encoding an N-terminal methionine at nucleotide positions 1–3. Nucleic acid molecules of the invention include those encoding the complete amino acid sequence excepting the N-terminal methionine shown in SEQ ID NO:2, which molecules also can encode additional amino acids fused to the N-terminus of the Synferon amino acid sequence.

Thus, one aspect of the invention provides an isolated polynucleotide comprising a nucleotide sequence selected from the group consisting of: (a) a nucleotide sequence encoding the Synferon polypeptide having the complete amino acid sequence in SEQ ID NO:2; (b) a nucleotide sequence encoding the Synferon polypeptide having the complete amino acid sequence in SEQ ID NO:2 excepting the N-terminal methionine (i.e., positions 2-161 of SEQ ID NO:2; and (c) a nucleotide sequence complementary to any of the nucleotide sequences in (a) or (b) above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b) or (c), above, or a polynucleotide which hybridizes under stringent hybridization conditions to a polynucleotide in (a), (b) or (c), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a Synferon polypeptide having an amino acid sequence in (a) or (b), above.

The present invention also relates to recombinant vectors, which include the isolated nucleic acid molecules of the present invention, and to host cells containing the recombinant vectors, as well as to methods of making such vectors and host cells and for using them for production of Synferon polypeptides or peptides by recombinant techniques.

The invention further provides an isolated Synferon polypeptide comprising an amino acid sequence selected from the group consisting of: (a) the amino acid sequence of the full-length Synferon polypeptide having the complete amino acid sequence shown in SEQ ID NO:2; and (b) the amino acid sequence of the full-length Synferon polypeptide having the complete amino acid sequence shown in SEQ ID NO:2 excepting the N-terminal methionine (i.e., positions 2 to 161 of SEQ ID NO:2). The polypeptides of the present invention also include polypeptides having an amino acid sequence at least 80% identical, more preferably at least 90% identical, and still more preferably 95%, 96%, 97%, 98% or 99% identical to those described in (a) or (b) above, as well as polypeptides having an amino acid sequence with at least 90% similarity, and more preferably at least 95% similarity, to those above. Polynucleotides encoding such polypeptides are also provided.

An additional embodiment of this aspect of the invention relates to a peptide or polypeptide which comprises the amino acid sequence of an epitope-bearing portion of a Synferon polypeptide having an amino acid sequence described in (a) or (b), above. Peptides or polypeptides having the amino acid sequence of an epitope-bearing portion of a Synferon polypeptide of the invention include portions of such polypeptides with at least six or seven, preferably at least nine, and more preferably at least about 30 amino acids to about 50 amino acids, although epitope-bearing polypeptides of any length up to and including the entire amino acid sequence of a polypeptide of the invention described above also are included in the invention.

In another embodiment, the invention provides an isolated antibody that binds specifically to a Synferon polypeptide having an amino acid sequence described in (a) or (b) above. The invention further provides methods for isolating antibodies that bind specifically to a Synferon polypeptide having an amino acid sequence as described herein. Such antibodies are useful therapeutically as described below.

The invention also provides for pharmaceutical compositions comprising Synferon polypeptides which may be employed, for instance, to treat immune system-related disorders such as viral infection, parasitic infection, bacterial infection, cancer, autoimmune disease, multiple sclerosis, lymphoma and allergy. Methods of treating individuals in need of interferon polypeptides are also provided.

The invention further provides compositions comprising a Synferon polynucleotide or a Synferon polypeptide for administration to cells in vitro, to cells ex vivo and to cells in vivo, or to a multicellular organism. In certain particularly preferred embodiments of this aspect of the invention, the compositions comprise a Synferon polynucleotide for expression of a Synferon polypeptide in a host organism for treatment of disease. Particularly preferred in this regard is expression in a human patient for treatment of a dysfunction associated with aberrant endogenous activity of an interferon.

The present invention also provides a screening method for identifying compounds capable of enhancing or inhibiting a biological activity of the Synferon polypeptide, which involves contacting a receptor which is enhanced by the Synferon polypeptide with the candidate compound in the presence of a Synferon polypeptide, assaying, for example, anti-viral activity in the presence of the candidate compound and the Synferon polypeptide, and comparing the activity to a standard level of activity, the standard being assayed when contact is made between the receptor and Synferon in the absence of the candidate compound. In this assay, an increase in activity over the standard indicates that the candidate compound is an agonist of Synferon activity and a decrease in activity compared to the standard indicates that the compound is an antagonist of Synferon activity.

An additional aspect of the invention is related to a method for treating an individual in need of an increased level of interferon activity in the body comprising administering to such an individual a composition comprising a therapeutically effective amount of an isolated Synferon polypeptide of the invention or an agonist thereof.

A still further aspect of the invention is related to a method for treating an individual in need of a decreased level of interferon activity in the body comprising, administering to such an individual a composition comprising a therapeutically effective amount of a Synferon antagonist. Preferred antagonists for use in the present invention are Synferon-specific antibodies.

BRIEF DESCRIPTION OF THE FIGURES

FIG. 1 shows the nucleotide sequence (SEQ ID NO:1) and amino acid sequence (SEQ ID NO:2) of Synferon.

FIG. 2 shows the regions of identity between the amino acid sequences of the Synferon protein and translation product of the human mRNA for Interferon Omega (SEQ ID NO:3), determined by the computer program Bestfit (Wisconsin Sequence Analysis Package, Version 8 for Unix, Genetics Computer Group, University Research Park, 575 Science Drive, Madison, Wis. 53711) using the default parameters.

FIG. 3 shows an analysis of the Synferon amino acid sequence. Alpha, beta, turn and coil regions; hydrophilicity and hydrophibicity; amphipathic regions; flexible regions; antigenic index and surface probability are shown. In the "Antigenic Index—Jameson-Wolf" graph, the positive peaks indicate locations of the highly antigenic regions of the Synferon protein, i.e., regions from which epitope-bearing peptides of the invention can be obtained.

DETAILED DESCRIPTION

The present invention provides isolated nucleic acid molecules comprising a polynucleotide encoding a Synferon polypeptide having the amino acid sequence shown in SEQ ID NO:2. The nucleotide sequence shown in FIG. 1 (SEQ ID NO:1) was obtained by sequencing the HKIXK74 pseudogene which is similar to IFN-omega and resolving naturally occuring mutations (e.g., frameshifts) in favor of an IFN consensus sequence. An synthetic DNA molecule "PF404" encoding Synferon was deposited on Dec. 9, 1997 at the American Type Culture Collection, 10801 University Boulevard, Manassas, Va. 20110-2209, and given accession number ATCC 209522. The deposited DNA is contained in the pHE4-5 plasmid, the production and expression of which is described in Example 1, below.

The Synferon protein of the present invention shares sequence homology with many members of the interferon family, most noteably the translation product of the human mRNA for IFN-omega (FIG. 2) (SEQ ID NO:3). IFN-omega has been shown to inhibit the proliferation of a variety of tumor cell lines in vitro, stimulate natural killer cell activity, enhance expression of major histocompatibility complex class I (but not class II) antigens and inhibit proliferation of lymphocytes stimulated with mitogens or allogeneic cells. Adolf, G. R., Human interferon omega—a review, *Mult Scler* 1995;1 Suppl 1:S44–S47.

The amino acid sequence of Synferon is based almost entirely on a naturally occuring pseudogene. Based on its homology to IFN-omega, Synferon is believed to share many of its biological activities, including, inhibition of tumor proliferation, antiviral activities, NK cell activiation, and immune system enhancement.

NUCLEIC ACID MOLECULES

By "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U).

Using the information provided herein, such as the nucleotide sequence in FIG. 1 (SEQ ID NO:1), a nucleic acid molecule of the present invention encoding a Synferon polypeptide may be obtained using standard molecular biology procedures, such as those for cloning DNAs.

The nucleotide sequence of the Synferon DNA of FIG. 1 (SEQ ID NO:1) contains an open reading frame encoding a protein of 161 amino acid residues, with an initiation codon at nucleotide positions 1–3 of the nucleotide sequence in FIG. 1 (SEQ ID NO:1). The amino acid sequence of the Synferon protein shown in SEQ ID NO:2 is about 55% identical to IFN-omega, (FIG. 2), which can be accessed through GenBank with Accession No. gb|A12140.

Leader and Mature Sequences

According to the signal hypothesis, once export of the growing protein chain across the rough endoplasmic reticulum has been initiated, proteins secreted by mammalian cells have a signal or secretory leader sequence which is cleaved from the complete polypeptide to produce a secreted "mature" form of the protein. Most mammalian cells and even insect cells cleave secreted proteins with the same specificity. However, in some cases, cleavage of a secreted protein is not entirely uniform, which results in two or more mature species of the protein. Further, it has long been known that the cleavage specificity of a secreted protein is ultimately determined by the primary structure of the complete protein, that is, it is inherent in the amino acid sequence of the polypeptide. The present invention provides a nucleotide sequence encoding a mature Synferon-polypeptide having the amino acid sequence shown in SEQ ID NO:2. As will be appreciated by those of skill in the art, it may be beneficial to provide an artificial leader sequence, such as one from a known gene, for selected secretion in eukaryotic cells. Secretory leader sequences are known to those of skill in the art.

As indicated, nucleic acid molecules of the present invention may be in the form of RNA, or in the form of DNA. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the, present invention. Isolated nucleic acid molecules according to the present invention further include such molecules produced synthetically.

Isolated nucleic acid molecules of the present invention include DNA molecules comprising an open reading frame (ORF) with an initiation codon at positions 1–3 of the nucleotide sequence shown in FIG. 1 (SEQ ID NO:1).

Also included are DNA molecules comprising the coding sequence for the Synferon protein lacking an N-terminal methionine shown at positions 2-161 of SEQ ID NO:2. Such polypeptides are useful for making N-terminal fusions, e.g., fused leader sequences.

In addition, isolated nucleic acid molecules of the invention include DNA molecules which comprise a sequence substantially different from those described above but which, due to the degeneracy of the genetic code, still encode the Synferon protein. Of course, the genetic code and species-specific codon preferences are well known in the art. Thus, it would be routine for one skilled in the art to generate the degenerate variants described above, for instance, to optimize codon expression for a particular host (e.g., change codons in the human mRNA to those preferred by a bacterial host such as *E. coli*).

The invention further provides an isolated nucleic acid molecule having the nucleotide sequence shown in FIG. 1 (SEQ ID NO:1) or the nucleotide sequence of the Synferon cDNA contained in the above-described deposited clone, or a nucleic acid molecule having a sequence complementary to one of the above sequences. Such isolated molecules, particularly DNA molecules, are useful for production of the Synferon polypeptide of the invention and as a probe for detection of mRNA in cells transfected with a vector for the purpose of producing Synferon; i.e., as a marker for determining expression of the heterologous gene in a host cell.

Further, the invention includes a polynucleotide comprising any portion of at least about 30 contiguous nucleotides, preferably at least about 50 contiguous nucleotides, of SEQ ID NO:1.

More generally, by a fragment of an isolated nucleic acid molecule having the nucleotide sequence of the deposited cDNA or the nucleotide sequence shown in FIG. 1 (SEQ ID NO:1) is intended fragments at least about 15 nt, and more preferably at least about 20 nt, still more preferably at least about 30 nt, and even more preferably, at least about 40 nt in length which are useful as diagnostic probes and primers as discussed herein. Of course, larger fragments 50–300 nt in length are also useful according to the present invention as are fragments corresponding to most, if not all, of the nucleotide sequence of the deposited cDNA or as shown in FIG. 1 (SEQ ID NO:1). By a fragment at least 20 nt in length, for example, is intended fragments which include 20 or more contiguous bases from the nucleotide sequence of the deposited cDNA or the nucleotide sequence as shown in FIG. 1 (SEQ ID NO:1). Preferred nucleic acid fragments of the present invention include nucleic acid molecules encoding epitope-bearing portions of the Synferon polypeptide as identified in FIG. 3 and described in more detail below.

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone contained in ATCC Deposit No. 209522. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30–70 (e.g., 50) nt of the reference polynucleotide. These are useful as diagnostic probes and primers as discussed above and in more detail below.

By a portion of a polynucleotide of "at least 20 nt in length," for example, is intended 20 or more contiguous nucleotides from the nucleotide sequence of the reference polynucleotide (e.g., the deposited cDNA or the nucleotide sequence as shown in FIG. 1 (SEQ ID NO:1)). Of course, a polynucleotide which hybridizes only to a poly A sequence (such as the 3' terminal poly(A) tract of the Synferon cDNA shown in FIG. 1 (SEQ ID NO:1)), or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone).

As indicated, nucleic acid molecules of the present invention which encode a Synferon polypeptide may include, but are not limited to those encoding the amino acid sequence of the complete polypeptide, by itself; and the coding sequence for the complete polypeptide and additional sequences, such as those encoding an added secretory leader sequence, such as a pre-, or pro- or prepro- protein sequence.

Also encoded by nucleic acids of the invention are the above protein sequences together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities.

Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821–824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37: 767 (1984). As discussed below, other such fusion proteins include the Synferon fused to Fc at the N- or C-terminus.

Variant and Mutant Polynucleotides

The present invention further relates to variants of the nucleic acid molecules of the present invention, which encode portions, analogs or derivatives of the Synferon protein. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the Synferon protein or portions thereof. Also especially preferred in this regard are conservative substitutions.

Further embodiments include an isolated nucleic acid molecule comprising a polynucleotide having a nucleotide sequence at least 90% identical, and more preferably at least 95%, 96%, 97%, 98% or 99% identical to a polynucleotide selected from the group consisting of: (a) a nucleotide sequence encoding the Synferon polypeptide having the complete amino acid sequence in SEQ ID NO:2; (b) a nucleotide sequence encoding the Synferon polypeptide having the complete amino acid sequence in SEQ ID NO:2 excepting the N-terminal methionine (i.e., positions 2–161 of SEQ ID NO:2; and (c) a nucleotide sequence complementary to any of the nucleotide sequences in (a) or (b) above.

Further embodiments of the invention include isolated nucleic acid molecules that comprise a polynucleotide having a nucleotide sequence at least 90% identical, and more preferably at least 95%, 96%, 97%, 98% or 99% identical, to any of the nucleotide sequences in (a), (b) or (c), above, or a polynucleotide which hybridizes under stringent hybridization conditions to a polynucleotide in (a), (b) or (c), above. This polynucleotide which hybridizes does not hybridize under stringent hybridization conditions to a polynucleotide having a nucleotide sequence consisting of only A residues or of only T residues. An additional nucleic acid embodiment of the invention relates to an isolated nucleic acid molecule comprising a polynucleotide which encodes the amino acid sequence of an epitope-bearing portion of a Synferon polypeptide having an amino acid sequence in (a) or (b), above.

The present invention also relates to recombinant vectors, which include the isolated nucleic acid molecules of the present invention, and to host cells containing the recombinant vectors, as well as to methods of making such vectors and host cells and for using them for production of Synferon polypeptides or peptides by recombinant techniques.

By a polynucleotide having a nucleotide sequence at least, for example, 95% "identical"to a reference nucleotide sequence encoding a Synferon polypeptide is intended that the nucleotide sequence of the polynucleotide is identical to the reference sequence except that the polynucleotide sequence may include up to five point mutations per each 100 nucleotides of the reference nucleotide sequence encoding the Synferon polypeptide. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mutations of the reference sequence may occur at the 5' or 3' terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 90%, 95%, 96%, 97%, 98% or 99% identical to, for instance, the nucleotide sequence shown in FIG. 1 or to the nucleotides sequence of the deposited DNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). Besffit uses the local homology algorithm of Smith and Waterman,*Advances in Applied Mathematics* 2:482–489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The present application is directed to nucleic acid molecules at least 90%, 95%, 96%, 97%, 98% or 99% identical to the nucleic acid sequence shown in FIG. 1 (SEQ ID NO:1) or to the nucleic acid sequence of the deposited DNA, irrespective of whether they encode a polypeptide having Synferon activity. This is because even where a particular nucleic acid molecule does not encode a polypeptide having Synferon activity, one of skill in the art would still know how to use the nucleic acid molecule, for instance, as a hybridization probe or a polymerase chain reaction (PCR) primer. Uses of the nucleic acid molecules of the present invention that do not encode a polypeptide having Synferon activity include, inter alia, isolating allelic variants in a cDNA library.

Preferred, however, are nucleic acid molecules having sequences at least 90%, 95%, 96%, 97%, 98% or 99% identical to the nucleic acid sequence shown in FIG. 1 (SEQ ID NO:1) or to the nucleic acid sequence of the deposited DNA which do, in fact, encode a polypeptide having Synferon protein activity. By "a polypeptide having Synferon activity" is intended polypeptides exhibiting activity similar, but not necessarily identical, to an activity of the Synferon protein of the invention, as measured in a particular biological assay. For example, the Synferon protein of the present invention inhibits bone marrow colony formation in-vitro and can be assayed according to the method of Tiefenthaler M. et al. (*Interferon Cytokine Res*, 1997 June; 17(6):327–329, incorporated herein by reference in its entirety). In addition, Synferon can inhibit GM-CSF induced proliferation of the erythroleukaemic cell line TF-1 according to the assays reported by Mire-Sluis A. R. et al. (*J. Immunol. Methods Sep.* 9, 1996;195(1–2):55–61, incorporated herein by reference). Alternatively, Synferon can be assayed for classical anti-viral activity by any of several assays known to those of skill in the art, for example, in the assay reported by Sugiyama, K. et al. (*Yakugaku Zasshi* 1995 May; 115(5):390–393).

The Synferon protein of the present invention inhibits bone marrow proliferation and shows anti-viral activity in a dose-dependent manner in the above-described assays. Thus, "a polypeptide having Synferon protein activity" includes polypeptides that also exhibit any of the same activities in the above-described assays in a dose-dependent manner. Although the degree of dose-dependent activity need not be identical to that of the Synferon protein, preferably, "a polypeptide having Synferon protein activity" will exhibit substantially similar dose-dependence in a given activity as compared to the Synferon protein (i.e., the candidate polypeptide will exhibit greater activity or not more than about 25-fold less and, preferably, not more than about tenfold less activity relative to the reference Synferon protein).

Of course, due to the degeneracy of the genetic code, one of ordinary skill in the art will immediately recognize that a large number of the nucleic acid molecules having a sequence at least 90%, 95%, 96%, 97%, 98%, or 99% identical to the nucleic acid sequence of the deposited cDNA or the nucleic acid sequence shown in FIG. 1 (SEQ ID NO:1) will encode a polypeptide "having Synferon protein activity." In fact, since degenerate variants of these nucleotide sequences all encode the same polypeptide, this will be clear to the skilled artisan even without performing the above described comparison assay. It will be further recognized in the art that, for such nucleic acid molecules that are not degenerate variants, a reasonable number will also encode a polypeptide having Synferon protein activity. This is because the skilled artisan is fully aware of amino acid substitutions that are either less likely or not likely to significantly effect protein function (e.g., replacing one aliphatic amino acid with a second aliphatic amino acid), as further described below.

Vectors and Host Cells

The present invention also relates to vectors which include the isolated DNA molecules of the present invention, host cells which are genetically engineered with the recombinant vectors, and the production of Synferon polypeptides or fragments thereof by recombinant techniques. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the *E. coli* lac, trp, phoA and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in *E. coli* and other bacteria. Representative examples of appropriate hosts include, but are not limited to, bacterial cells, such as *E. coli*, Streptomyces and *Salmonella typhimurium* cells; fungal cells, such as yeast cells; insect cells such as Drosophila S2 and Spodoptera Sf9 cells; animal cells such as CHO, COS, 293 and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc., supra; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology* (1986).

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. A preferred fusion protein comprises a heterologous region from immunoglobulin that is useful to stabilize and purify proteins. For example, EP-A-O 464 533 (Canadian counterpart 2045869) discloses fusion proteins comprising various portions of constant region of immunoglobulin molecules together with another human protein or part thereof. In many cases, the Fc part in a fusion protein is thoroughly advantageous for use in therapy and diagnosis and thus results, for example, in improved pharmacokinetic properties (EP-A 0232 262). On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as hIL-5, have been fused with Fc portions for the purpose of high-throughput screening assays to identify antagonists of hIL-5. See, D. Bennett et al., *J. Molecular Recognition* 8:52–58 (1995) and K. Johanson et al., *J. Biol. Chem.* 270:9459–9471 (1995).

The Synferon protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins this prokaryotic removal process is inefficient, depending on the nature of the amino acid to which the N-terminal methionine is covalently linked.

POLYPEPTIDES AND FRAGMENTS

The invention further provides an isolated Synferon polypeptide having the amino acid sequence encoded by the deposited DNA, or the amino acid sequence in SEQ ID NO:2, or a peptide or polypeptide comprising a portion of the above polypeptides.

Variant and Mutant Polypeptides

To improve or alter the characteristics of Synferon polypeptides, protein engineering may be employed. Recombinant DNA technology known to those skilled in the art can be used to create novel mutant proteins or "muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

N-Terminal and C-Terminal Deletion Mutants

For instance, for many proteins, including the extracellular domain of a membrane associated protein or the mature form(s) of a secreted protein, it is known in the art that one or more amino acids may be deleted from the N-terminus or C-terminus without substantial loss of biological function. For instance, Ron et al., *J. Biol. Chem.*, 268:2984–2988 (1993) reported modified KGF proteins that had heparin binding activity even if 3, 8, or 27 amino-terminal amino acid residues were missing. In the present case, since the protein of the invention is a member of the interferon polypeptide family, deletions of N-terminal amino acids up to the Cysteine at position 2 as shown in SEQ ID NO:2 may retain some biological activity such as antiviral activity or inhibition of bone marrow proliferation. Polypeptides having further N-terminal deletions including the Cys-2 residue in SEQ ID NO:2 would not be expected to retain such biological activities because it is known that this residue in an interferon-related polypeptide is required for forming a disulfide bridge to provide structural stability which is needed for receptor binding and signal transduction.

However, even if deletion of one or more amino acids from the N-terminus of a protein results in modification of loss of one or more biological functions of the protein, other biological activities may still be retained. Thus, the ability of the shortened protein to induce and/or bind to antibodies which recognize the complete protein generally will be retained when less than the majority of the residues of the complete protein are removed from the N-terminus. Whether a particular polypeptide lacking N-terminal residues of a complete protein retains such immunologic activities can readily be determined by routine methods described herein and otherwise known in the art.

Accordingly, the present invention further provides polypeptides having one or more residues deleted from the amino terminus of the amino acid sequence of the Synferon shown in SEQ ID NO:2, up to the Cys-2, and polynucleotides encoding such polypeptides. In particular, the present invention provides polypeptides comprising the amino acid sequence of residues n-161 of SEQ ID NO:2, where n is an integer in the range of 1–2 and where Cys-2 is the position of the first residue from the N-terminus of the complete Synferon polypeptide (shown in SEQ ID NO:2) believed to be required for activity of the Synferon protein.

More in particular, the invention provides polynucleotides encoding polypeptides having the amino acid sequence of residues 1–161, 2–161 and 3–161 of SEQ ID NO:2. Polynucleotides encoding these polypeptides also are provided.

Similarly, many examples of biologically functional C-terminal deletion muteins are known. For instance, Interferon gamma shows up to ten times higher activities by deleting 8–10 amino acid residues from the carboxy terminus of the protein (Döbeli et al., *J. Biotechnology* 7:199–216 (1988). In the present case, since the protein of the invention is a member of the interferon polypeptide family, deletions of C-terminal amino acids up to the Valine at position 141 in SEQ ID NO:2 may retain some biological activity such as antiviral activity or inhibition of bone marrow proliferation. Polypeptides having further C-terminal deletions including Val-141 of SEQ ID NO:2 would not be expected to retain such biological activities because it is known that this residue in an interferon-related polypeptide is conserved among many members and is thought to be important for receptor binding and signal transduction.

However, even if deletion of one or more amino acids from the C-terminus of a protein results in modification of loss of one or more biological functions of the protein, other biological activities may still be retained. Thus, the ability of the shortened protein to induce and/or bind to antibodies which recognize the complete protein generally will be retained when less than the majority of the residues of the complete protein are removed from the C-terminus. Whether a particular polypeptide lacking C-terminal residues of a complete protein retains such immunologic activities can readily be determined by routine methods described herein and otherwise known in the art.

Accordingly, the present invention further provides polypeptides having one or more residues from the carboxy terminus of the amino acid sequence of the Synferon shown in SEQ ID NO:2, up to Val-141 of SEQ ID NO:2, and polynucleotides encoding such polypeptides. In particular, the present invention provides polypeptides having the amino acid sequence of residues 1-m of the amino acid sequence in SEQ ID NO:2, where m is any integer in the range of 141–161 and residue Val-141 is the position of the first residue from the C-terminus of the complete Synferon polypeptide (shown in SEQ ID NO:2) believed to be required for activity of the Synferon protein.

More in particular, the invention provides polynucleotides encoding polypeptides having the amino acid sequence of residues 1–141, 1–142, 1–143, 1–144, 1–145, 1–146, 1–147, 1–148, 1–149, 1–150, 1–151, 1–152, 1–153, 1–154, 1–155, 1–156, 1–157, 1–158, 1–159, 1–160, and 1–161 of SEQ ID NO:2. Polynucleotides encoding these polypeptides also are provided.

The invention also provides polypeptides having one or more amino acids deleted from both the amino and the carboxyl termini, which may be described generally as having residues n-m of SEQ ID NO:2, where n and m are integers as described above. Furthermore, the invention provides these mutant polypeptides optionally having an N-terminal methionine. The polypeptides may therefore also be described by the formula x-n-m where X is either $NH_2$ or Met and n and m are integers as described above. Polynucleotides encoding these polypeptides are, of course, also provided.

Other Mutants

In addition to terminal deletion forms of the protein discussed above, it also will be recognized by one of ordinary skill in the art that some amino acid sequences of the Synferon polypeptide can be varied without significant effect on the structure or function of the protein. If such differences in sequence are contemplated, it should be remembered that there will be critical areas on the protein which determine activity.

Thus, the invention further includes variations of the Synferon polypeptide which show substantial Synferon polypeptide activity or which include regions of Synferon protein such as the protein portions discussed below. Such mutants include deletions, insertions, inversions, repeats, and type substitutions selected according to general rules known in the art so as have little effect on activity. For example, guidance concerning how to make phenotypically silent amino acid substitutions is provided in Bowie, J. U. et al., "Deciphering the Message in Protein Sequences: Tolerance to Amino Acid Substitutions," *Science* 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality.

As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U. et al., supra, and the references cited therein. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe, Tyr.

Thus, the fragment, derivative or analog of the polypeptide of SEQ ID NO:2, or that encoded by the deposited cDNA, may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the Synferon polypeptide is fused with another compound, such as a compound to increase the half-life of the polypeptide (for example, polyethylene glycol), or (iv) one in which the additional amino acids are fused to the above form of the polypeptide, such as an IgG Fc fusion region peptide or leader or secretory sequence or a sequence which is employed for purification of the above form of the polypeptide or a proprotein sequence. Such fragments, derivatives and analogs are deemed to be within the scope of those skilled in the art from the teachings herein Thus, the Synferon of the present invention may include one or more amino acid substitutions, deletions or additions, either from natural mutations or human manipulation. As indicated, changes are preferably of a minor nature, such as conservative amino acid substitutions that do not significantly affect the folding or activity of the protein.

Amino acids in the Synferon protein of the present invention that are essential for function can be identified by methods known in the art, such as site-directed mutagenesis or alanine-scanning mutagenesis (Cunningham and Wells, *Science* 244:1081–1085 (1989)). The latter procedure introduces single alanine mutations at every residue in the molecule. The resulting mutant molecules are then tested for biological activity such as receptor binding or in vitro or in vitro proliferative activity.

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic (Pinckard et al., *Clin. Exp. Immunol.* 2:331–340 (1967); Robbins et al., *Diabetes* 36: 838–845 (1987); Cleland et al., *Crit. Rev. Therapeutic Drug Carrier Systems* 10:307–377 (1993).

Replacement of amino acids can also change the selectivity of the binding of a ligand to cell surface receptors. For example, Ostade et al., *Nature* 361:266–268 (1993) describes certain mutations resulting in selective binding of TNF-α to only one of the two known types of TNF receptors. Sites that are critical for ligand-receptor binding can also be determined by structural analysis such as crystallization, nuclear magnetic resonance or photoaffinity labeling (Smith et al., *J. Mol. Biol.* 224:899–904 (1992) and de Vos et al. *Science* 255:306–312 (1992)).

The polypeptides of the present invention are preferably provided in an isolated form, and preferably are substantially purified. A recombinantly produced version of the Synferon polypeptide can be substantially purified by the one-step method described in Smith and Johnson, *Gene* 67:31–40 (1988). Polypeptides of the invention also can be purified from natural or recombinant sources using anti-Synferon antibodies of the invention in methods which are well known in the art of protein purification.

The invention further provides an isolated Synferon polypeptide comprising an amino acid sequence selected from the group consisting of: (a) the amino acid sequence of the full-length Synferon polypeptide having the complete amino acid sequence shown in SEQ ID NO:2; and (b) the amino acid sequence of the full-length Synferon polypeptide having the complete amino acid sequence shown in SEQ ID NO:2 excepting the N-terminal methionine (i.e., positions 2–161 of SEQ ID NO:2).

Further polypeptides of the, present invention include polypeptides which have at least 90% similarity, more preferably at least 95% similarity, and still more preferably at least 96%, 97%, 98% or 99% similarity to those described above. The polypeptides of the invention also comprise those which are at least 80% identical, more preferably at least 90% or 95% identical, still more preferably at least 96%, 97%, 98% or 99% identical to the polypeptide encoded by the deposited DNA or to the polypeptide of SEQ ID NO:2, and also include portions of such polypeptides with at least 30 amino acids and more preferably at least 50 amino acids. Polynucleotides encoding such polypeptides are also provided.

By "% similarity" for two polypeptides is intended a similarity score produced by comparing the amino acid sequences of the two polypeptides using the Bestfit program (Wisconsin Sequence Analysis Package, Version 8 for Unix, Genetics Computer Group, University Research Park, 575 Science Drive, Madison, Wis. 53711) and the default settings for determining similarity. Bestfit uses the local homology algorithm of Smith and Waterman (Advances in Applied Mathematics 2:482–489, 1981) to find the best segment of similarity between two sequences.

By a polypeptide having an amino acid sequence at least, for example, 95% "identical" to a reference amino acid sequence of a Synferon polypeptide is intended that the amino acid sequence of the polypeptide is identical to the reference sequence except that the polypeptide sequence may include up to five amino acid alterations per each 100 amino acids of the reference amino acid of the Synferon polypeptide. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 90%, 95%, 96%, 97%, 98% or 99% identical to, for instance, the amino acid sequence shown in SEQ ID NO:2 or to the amino acid sequence encoded by deposited DNA clone can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

The polypeptide of the present invention could be used as a molecular weight marker on SDS-PAGE gels or on molecular sieve gel filtration columns using methods well known to those of skill in the art.

As described in detail below, the polypeptides of the present invention can also be used to raise polyclonal and monoclonal antibodies, which are useful in assays for detecting Synferon protein expression as described below or as agonists and antagonists capable of enhancing or inhibiting Synferon protein function. Further, such polypeptides can be used in the yeast two-hybrid system to "capture" Synferon protein binding proteins which are also candidate agonists and antagonists according to the present invention. The yeast two hybrid system is described in Fields and Song, Nature 340:245–246 (1989).

Epitope-Bearing Portions

In another aspect, the invention provides a peptide or polypeptide comprising an epitope-bearing portion of a polypeptide of the invention. The epitope of this polypeptide portion is an immunogenic or antigenic epitope of a polypeptide of the invention. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., Proc. Natl. Acad. Sci. USA 81:3998–4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, Sutcliffe, J. G., Shinnick, T. M., Green, N. and Learner, R. A. (1983) "Antibodies that react with predetermined sites on proteins," Science, 219:660–666. Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals. Antigenic epitope-bearing peptides and polypeptides of the invention are therefore useful to raise antibodies, including monoclonal antibodies, that bind specifically to a polypeptide of the invention. See, for instance, Wilson et al., Cell 37:767–778 (1984) at 777.

Antigenic epitope-bearing peptides and polypeptides of the invention preferably contain a sequence of at least seven, more preferably at least nine and most preferably between about 15 to about 30 amino acids contained within the amino acid sequence of a polypeptide of the invention. Non-limiting examples of antigenic polypeptides or peptides that can be used to generate Synferon-specific antibodies include: a polypeptide comprising amino acid residues from about Asp 3 to about Val 17 in SEQ ID NO:2; a polypeptide comprising amino acid residues from about Gln 21 to about Thr 54 in SEQ ID NO:2; a polypeptide comprising amino acid residues from about Asn 70 to about Thr 86 in SEQ ID NO:2; a polypeptide comprising amino acid residues from about Thr 114 to about Val 118 in SEQ ID NO:2; a polypeptide comprising amino, acid residues Glu 130 to about Cys 137 in SEQ ID NO:2; and a polypeptide comprising amino acid residues Ala 143 to about Val 157 in SEQ ID NO:2. These polypeptide fragments have been determined to bear antigenic epitopes of the Synferon protein by the analysis of the Jameson-Wolf antigenic index, as shown in FIG. 3, above.

The epitope-bearing peptides and polypeptides of the invention may be produced by any conventional means. See, e.g., Houghten, R. A. (1985) "General method for the rapid solid-phase synthesis of large numbers of peptides: specificity of antigen-antibody interaction at the level of individual amino acids." Proc. Natl. Acad. Sci. USA 82:5131–5135; this "Simultaneous Multiple Peptide Synthesis (SMPS)" process is further described in U.S. Pat. No. 4,631,211 to Houghten et al. (1986).

Epitope-bearing peptides and polypeptides of the invention are used to induce antibodies according to methods well known in the art. See, for instance, Sutcliffe et al., supra; Wilson et al., supra; Chow, M. et al., Proc. Natl. Acad. Sci. USA 82:910–914; and Bittle, F. J. et al., J. Gen. Virol. 66:2347–2354 (1985). Immunogenic epitope-bearing peptides of the invention, i.e., those parts of a protein that elicit an antibody response when the whole protein is the inmmunogen, are identified according to methods known in the art. See, for instance, Geysen et al., supra. Further still, U.S. Pat. No. 5,194,392 to Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, U.S. Pat. No. 4,433,092 to Geysen (1989) describes a method of detecting or determining a sequence of monomers which is a topographical equivalent of a ligand which is complementary to the ligand binding site of a particular receptor of interest. Similarly, U.S. Pat. No. 5,480,971 to Houghten, R. A. et al. (1996) on Peralkylated Oligopeptide Mixtures discloses linear C1–C7-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides of the invention also can be made routinely by these methods.

Fusion Proteins

As one of skill in the art will appreciate, Synferon polypeptides of the present invention and the epitope-bearing fragments thereof described above can be combined with parts of the constant domain of immunoglobulin (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulin (EP A 394,827; Traunecker et al., Nature 331:84–86 (1988)). Fusion proteins that have a disulfide-linked dimeric structure due to the IgG part can also be more efficient in binding and neutralizing other molecules than the monomeric Synferon protein or protein fragment alone (Fountoulakis et al., J. Biochem. 270:3958–3964 (1995)).

Antibodies

Synferon-protein specific antibodies for use in the present invention can be raised against the intact Synferon protein or an antigenic polypeptide fragment thereof, which may be presented together with a carrier protein, such as an albumnin, to an animal system (such as rabbit or mouse) or, if it is long enough (at least about 25 amino acids), without a carrier.

As used herein, the term "antibody" (Ab) or "monoclonal antibody" (Mab) is meant to include intact molecules as well as antibody fragments (such as, for example, Fab and F(ab')2 fragments) which are capable of specifically binding to Synferon protein. Fab and F(ab')2 fragments lack the Fc fragment of intact antibody, clear more rapidly from the circulation, and may have less non-specific tissue binding of an intact antibody (Wahl et al., *J. Nucl. Med.* 24:316–325 (1983)). Thus, these fragments are preferred.

The antibodies of the present invention may be prepared by any of a variety of methods. For example, cells expressing the Synferon protein or an antigenic fragment thereof can be administered to an animal in order to induce the production of sera containing polyclonal antibodies. In a preferred method, a preparation of Synferon protein is prepared and purified to render it substantially free of natural contaminants. Such a preparation is then introduced into an animal in order to produce polyclonal antisera of greater specific activity.

In the most preferred method, the antibodies of the present invention are monoclonal antibodies (or Synferon protein binding fragments thereof). Such monoclonal antibodies can be prepared using hybridoma technology (Köhler et al., *Nature* 256:495 (1975); Köhler et al., *Eur. J. Immunol.* 6:511 (1976); Köhler et al., Eur. J. Immunol. 6:292 (1976); Hammerling et al., in: *Monoclonal Antibodies and T-Cell Hybridomas*, Elsevier, N.Y., (1981) pp. 563–681). In general, such procedures involve immunizing an animal (preferably a mouse) with a Synferon protein antigen or, more preferably, with a Synferon protein-expressing cell. Suitable cells can be recognized by their capacity to bind anti-Synferon protein antibody. Such cells may be cultured in any suitable tissue culture medium; however, it is preferable to culture cells in Earle's modified Eagle's medium supplemented with 10% fetal bovine serum (inactivated at about 56° C.), and supplemented with about 10 g/l of nonessential amino acids, about 1,000 U/ml of penicillin, and about 100 µg/ml of streptomycin. The splenocytes of such mice are extracted and fused with a suitable myeloma cell line. Any suitable myeloma cell line may be employed in accordance with the present invention; however, it is preferable to employ the parent myeloma cell line (SP2O), available from the American Type Culture Collection, 10801 University Boulevard, Manassas, Va. 20110-2209. After fusion, the resulting hybridoma cells are selectively maintained in HAT medium, and then cloned by limiting dilution as described by Wands et al. (Gastroenterology 80:225–232 (1981)). The hybridoma cells obtained through such a selection are then assayed to identify clones which secrete antibodies capable of binding the Synferon protein antigen.

Alternatively, additional antibodies capable of binding to the Synferon protein antigen may be produced in a two-step procedure through the use of anti-idiotypic antibodies. Such a method makes use of the fact that antibodies are themselves antigens, and that, therefore, it is possible to obtain an antibody which binds to a second antibody. In accordance with this method, Synferon-protein specific antibodies are used to immunize an animal, preferably a mouse. The splenocytes of such an animal are then used to produce hybridoma cells, and the hybridoma cells are screened to identify clones which produce an antibody whose ability to bind to the Synferon protein-specific antibody can be blocked by the Synferon protein antigen. Such antibodies comprise anti-idiotypic antibodies to the Synferon protein-specific antibody and can be used to immunize an animal to induce formation of further Synferon protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, Synferon protein-binding fragments can be produced through the application of recombinant DNA technology or through synthetic chemistry.

For in vivo use of anti-Synferon in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. See, for review, Morrison, *Science* 229:1202 (1985); Oi et al., *BioTechniques* 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., *Nature* 312:643 (1984); Neuberger et al., *Nature* 314:268 (1985).

IMMUNE SYSTEM-RELATED DISORDERS

Treatment

It will also be appreciated by one of ordinary skill that, since the Synferon protein of the invention is a member of the interferon family, when Synferon is added to cells, tissues or the body of an individual, the protein will exert its physiological activities on its target cells of that individual. Therefore, it will be appreciated that conditions caused by a decrease in the standard or normal level of interferon activity in an individual, particularly disorders of the immune system, can be treated by administration of the Synferon polypeptide. Thus, the invention also provides a method of treatment of an individual in need of an increased level of interferon activity comprising administering to such an individual a pharmaceutical composition comprising an amount of an isolated Synferon polypeptide of the invention, effective to increase the interferon activity level in such an individual.

The human class I IFN receptor complex which mediates the biological activity of IFN-alpha and IFN-beta also binds IFN-omega and is expected to bind Synferon. Accordingly, Synferon can be used clinically for anti-viral therapy, for example, in the treatment of AIDS, viral hepatitis including chronic hepatitis B, hepatitis C, papilloma viruses, viral encephalitis, and in the prophylaxis of rhinitis and respiratory infections.

Synferon is also useful in the treatement of numerous cancers (e.g., hairy cell leukemia, acute myeloid leukemia, osteosarcoma, basal cell carcinoma, glioma, renal cell carcinoma, multiple myeloma, melanoma, and Hodgkin's disease).

Synferon is believed to stimulate natural killer cell activity. Accordingly, Synferon may be used to treat parasitic and bacterial infection for example, for treating *Cryptosporidium parvum* infection and multidrug-resistant pulmonary tuberculosis.

Synferon is also believed to be useful as an immunotherapeutic agent, more specifically as an immunosuppressive agent. For example, Synferon is believed to inhibit proliferation of lymphocytes stimulated with mitogens or allogeneic cells, myeloid progenitor cells and other bone marrow cells. Accordingly, Synferon is useful as a protective agent when administered prior to chemotherapy and in addition can be used to treat hyperproliferation of lymphocytes, myeloid progenitors and bone marrow stem cells, e.g., in the treatment of chronic myelogenous leukemia. Synferon polypeptides can also be used in the prevention of graft vs. host rejection, or to curtail the progresion of autoimmune diseases, such as arthritis, multiple sclerosis, (2) or diabetes (3). Synferon is also useful in the treatment of allergies in mammals, e.g., by inhibiting the humoral response.

Synferon may be used as an adjuvant or coadjuvant to enhance or simulate the immune response in cases of prophylactic or therapeutic vaccination.

Further, there is provided a method of treating infection in a patient comprising administering an effective amount of a polypeptide of the invention to a patient in need of anti-infective therapy. In a preferred embodiment the infection is of viral, bacterial, or parasitic etiology. In a particularly preferred embodiment, the infection is a viral infection.

Further, there is provided a method of treating cancer in a patient comprising administerin an effective amount of a polypeptide of the invention to a patient in need of anti-cancer therapy.

Further, there is provided a method of immunotherapy in a patient comprising administering an effective amount of a polypeptide of the invention to a patient in need of immunotherapy.

Formulations

The Synferon polypeptide composition will be formulated and dosed in a fashion consistent with good medical practice, taking into account the clinical condition of the individual patient (especially the side effects of treatment with Synferon polypeptide alone), the site of delivery of the Synferon polypeptide composition, the method of administration, the scheduling of administration, and other factors known to practitioners. The "effective amount" of Synferon polypeptide for purposes herein is thus determined by such considerations.

As a general proposition, the total pharmaceutically effective amount of Synferon polypeptide administered parenterally per dose will be in the range of about 1 $\mu$g/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the Synferon polypeptide is typically administered at a dose rate of about 1 $\mu$g/kg/hour to about 50 $\mu$g/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Pharmaceutical compositions containing the Synferon of the invention may be administered orally, rectally, parenterally, intracistemally, intravaginally, intraperitoneally, topically (as by powders, ointments, drops or transdermal patch), bucally, or as an oral or nasal spray. By "pharmaceutically acceptable carrier" is meant a non-toxic solid, semisolid or liquid filler, diluent, encapsulating material or formulation auxiliary of any type. The term "parenteral"as used herein refers to modes of administration which include intravenous, intramuscular, intraperitoneal, intrasternal, subcutaneous and intraarticular injection and infusion.

The Synferon polypeptide is also suitably administered by sustained-release systems. Suitable examples of sustained-release compositions include semi-permeable polymer matrices in the form of shaped articles, e.g., films, or mirocapsules. Sustained-release matrices include polylactides (U.S. Pat. No. 3,773,919, EP 58,481), copolymers of L-glutamic acid and gamma-ethyl-L-glutamate (Sidman, U. et al., *Biopolymers* 22:547–556 (1983)), poly (2-hydroxyethyl methacrylate) (R. Langer et al., *J. Biomed. Mater. Res.* 15:167–277 (1981), and R. Langer, *Chem. Tech.* 12:98–105 (1982)), ethylene vinyl acetate (R. Langer et al., Id.) or poly-D-(–)-3-hydroxybutyric acid (EP 133,988). Sustained-release Synferon polypeptide compositions also include liposomally entrapped Synferon polypeptide. Liposomes containing Synferon polypeptide are prepared by methods known per se: DE 3,218,121; Epstein et al., Proc. Natl. Acad. Sci. (USA) 82:3688–3692 (1985); Hwang et al., Proc. Natl. Acad. Sci. (USA) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal Synferon polypeptide therapy.

For parenteral administration, in one embodiment, the Synferon polypeptide is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to polypeptides.

Generally, the formulations are prepared by contacting the Synferon polypeptide uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulin; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The Synferon polypeptide is typically formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of Synferon polypeptide salts.

Synferon polypeptide to be used for therapeutic administration must be sterile. Sterility is readily accomplished by filtration through sterile filtration membranes (e.g., 0.2 micron membranes). Therapeutic Synferon polypeptide compositions generally are placed into a container having a sterile access port, for example, an intravenous solution bag or vial having a stopper pierceable by a hypodermic injection needle.

Synferon polypeptide ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous Synferon polypeptide solution, and the resulting mixture is lyophilized. The infusion solution is prepared by reconstituting the lyophilized Synferon polypeptide using bacteriostatic Water-for-Injection.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the polypeptides of the present invention may be employed in conjunction with other therapeutic compounds.

Agonists and Antagonists—Assays and Molecules

The invention also provides a method of screening compounds to identify those which enhance or block the action of Synferon on cells, such as its interaction with Synferon-binding molecules such as receptor molecules. An agonist is a compound which increases the natural biological functions of Synferon or which functions in a manner similar to Synferon, while antagonists decrease or eliminate such functions.

In another aspect of this embodiment the invention provides a method for identifying a receptor protein or other ligand-binding protein which binds specifically to a Synferon polypeptide. For example, a cellular compartment, such as a membrane or a preparation thereof, may be prepared from a cell that expresses a molecule that binds Synferon. The preparation is incubated with labeled Synferon. Synferon and complexes of Synferon bound to the receptor or other binding protein are isolated and characterized according to routine methods known in the art. Alternatively, the Synferon polypeptide may be bound to a solid support so that binding molecules solubilized from cells are bound to the column and then eluted and characterized according to routine methods.

In the assay of the invention for agonists or antagonists, a cellular compartment, such as a membrane or a preparation thereof, may be prepared from a cell that expresses a molecule that binds Synferon, such as a molecule of a signaling or regulatory pathway modulated by Synferon. The preparation is incubated with labeled Synferon in the absence or the presence of a candidate molecule which may be a Synferon agonist or antagonist. The ability of the candidate molecule to bind the binding molecule is reflected in decreased binding of the labeled ligand. Molecules which bind gratuitously, i.e., without inducing the effects of Synferon on binding the Synferon binding molecule, are most likely to be good antagonists. Molecules that bind well and elicit effects that are the same as or closely related to Synferon are agonists.

Synferon-like effects of potential agonists and antagonists may by measured, for instance, by determining activity of a second messenger system following interaction of the candidate molecule with a cell or appropriate cell preparation, and comparing the effect with that of Synferon or molecules that elicit the.same effects as Synferon. Second messenger systems that may be useful in this regard include but are not limited to AMP guanylate cyclase, ion channel or phosphoinositide hydrolysis second messenger systems.

Another example of an assay for Synferon antagonists is a competitive assay that combines Synferon and a potential antagonist with membrane-bound Synferon receptor molecules or recombinant Synferon receptor molecules under appropriate conditions for a competitive inhibition assay. Synferon can be labeled, such as by radioactivity, such that the number of Synferon molecules bound to a receptor molecule can be determined accurately to assess the effectiveness of the potential antagonist.

Potential antagonists include small organic molecules, peptides, polypeptides and antibodies that bind to a polypeptide of the invention and thereby inhibit or extinguish its activity. Potential antagonists also may be small organic molecules, a peptide, a polypeptide such as a closely related protein or antibody that binds the same sites on a binding molecule, such as a receptor molecule, without inducing Synferon-induced activities, thereby preventing the action of Synferon by excluding Synferon from binding.

Other potential antagonists include antisense molecules. Antisense technology can be used to control gene expression through antisense DNA or RNA or through triple-helix formation. Antisense techniques are discussed, for example, in Okano, *J. Neurochem.* 56: 560 (1991); "Oligodeoxynucleotides as Antisense Inhibitors of Gene Expression." CRC Press, Boca Raton, Fla. (1988). Triple helix formation is discussed in, for instance Lee et al., *Nucleic Acids Research* 6: 3073 (1979); Cooney et al., *Science* 241: 456 (1988); and Dervan et al., *Science* 251: 1360 (1991). The methods are based on binding of a polynucleotide to a complementary DNA or RNA. For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of Synferon. The antisense RNA oligonucleotide hybridizes to the mRNA in vivo and blocks translation of the mRNA molecule into Synferon polypeptide. The oligonucleotides described above can also be delivered to cells such that the antisense RNA or DNA may be expressed in vivo to inhibit production of Synferon protein.

The agonists and antagonists may be employed in a composition with a pharmaceutically acceptable carrier, e.g., as described above.

The antagonists may be employed for instance to inhibit interferon activity, for example, following chemotherapy to stimulate proliferation of bone marrow and haematopoietic progenitor cells. Any of the above antagonists may be employed in a composition with a pharmaceutically acceptable carrier, e.g., as hereinafter described.

Having generally described the invention, the same will be more readily understood by reference to the following examples, which are provided by way of illustration and are not intended as limiting.

EXAMPLES

Example 1

Cloning and Expression of Synferon in *E. coli*

The novel pHE4 series of bacterial expression vectors, in particular, the pHE4-5 vector is used for bacterial expression in this example. (QIAGEN, Inc., 9259 Eton Avenue, Chatsworth, Calif., 91311). pHE4-5/Synferon vector plasmid DNA contains the Synferon coding polynucleotide shown in FIG. 1 inserted between unique restriction enzyme sites NdeI and Asp718. The construct was deposited with the American Type Culture Collection, 10801 University Boulevard, Manassas, Va. 20110-2209, on Dec. 9, 1997 and given Accession No 209522, as a convenience to those of skill in the art.

The pHE4-5 bacterial expression vector includes a neomycin phosphotransferase gene for selection, an *E. coli* origin of -replication, a T5 phage promoter sequence, two lac operator sequences, a Shine-Delgarno sequence, and the lactose operon repressor gene (lacIq). These elements are arranged such that an inserted DNA fragment encoding a polypeptide expresses that polypeptide with the six His residues (i.e., a "6×His tag") covalently linked to the amino terminus of that polypeptide.

The DNA sequence encoding the mature Synferon protein was amplified using PCR oligonucleotide primers which anneal to the amino terminal sequences of the desired portion of the Synferon protein and to sequences in the deposited construct 3' to the cDNA coding sequence. Additional nucleotides containing restriction sites to facilitate cloning in the pHE4-5 vector were added to the 5' and 3' primer sequences, respectively.

For cloning the Synferon protein coding region, the 5' primer has the sequence 5' GGGAATTC CATATGTGCGACCTGCCGGAAACCCA 3' (SEQ ID NO:4) containing the underlined NdeI restriction site. One of ordinary skill in the art would appreciate, of course, that the point in the protein coding sequence where the 5' primer begins may be varied to amplify a DNA segment encoding any desired portion of the complete Synferon protein. The 3' primer has the sequence 5' GCGCC GGTACCCTAAGCGATCAGACGAACCTGCAGGTTAG 3' (SEQ ID NO:5) containing the underlined Asp718 restriction site.

The amplified Synferon DNA fragment was digested with NdeI and Asp718 and it and the linearized plasmid were then ligated together. Insertion of the Synferon DNA into the restricted pHE4-5 vector places the Synferon protein coding region downstream from the IPTG-inducible promoter and in-frame with an initiating AUG and the six histidine codons.

The ligation mixture is transformed into competent *E. coli* cells using standard procedures such as those described by Sambrook and colleagues (*Molecular Cloning: a Laboratory Manual, 2nd Ed.*; Cold Spring Harbor Laboratory Press, Cold Spring Harbor, N.Y. (1989)). *E. coli* strain M15/rep4, containing multiple copies of the plasmid pREP4, which expresses the lac repressor and confers kanamycin resistance ("Kanr"), is used in carrying out the illustrative example described herein. This strain, which is only one of many that are suitable for expressing Synferon protein, is available commercially (QIAGEN, Inc., supra). Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 $\mu$g/ml) and kanamycin (25 $\mu$g/ml). The O/N culture is used to inoculate a large culture, at a dilution of approximately 1:25 to 1:250. The cells are grown to an optical density at 600 nm ("OD600") of between 0.4 and 0.6. Isopropyl-$\beta$-D-thiogalactopyranoside ("IPTG") is then added to a final concentration of 1 mM to induce transcription from the lac repressor sensitive promoter, by inactivating the lacIq repressor. Cells subsequently are incubated further for 3 to 4 hours. Cells then are harvested by centrifugation.

The cells are then stirred for 3–4 hours at 4° C. in 6M guanidine-HCl, pH 8. The cell debris is removed by centrifugation, and the supernatant containing the Synferon polypeptide is loaded onto a nickel-nitrilo-tri-acetic acid ("Ni-NTA") affinity resin column (QIAGEN, Inc., supra). Proteins with a 6×His tag bind to the Ni-NTA resin with high affinity and can be purified in a simple one-step procedure (for details see: The QIAexpressionist, 1995, QIAGEN, Inc., supra). Briefly the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the Synferon is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins can be eluted by the addition of 250 mM immidazole. Imindazole is removed by a final dialyzing step against PBS or 50 mM sodium acetate pH 6 buffer plus 200 mM NaCl. The purified protein is stored at 4° C. or frozen at –80° C.

The following alternative method may be used to purify Synferon expressed in *E coli* when it is present in the form of inclusion bodies. Unless otherwise specified, all of the following steps are conducted at 4–10° C.

Upon completion of the production phase of the *E. coli* fermentation, the cell culture is cooled to 4–10° C. and the cells are harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells ware then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the Synferon polypeptide-containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4° C. without mixing for 12 hours prior to further purification steps.

To clarify the refolded Synferon polypeptide solution, a previously prepared tangential filtration unit equipped with 0.16 μm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 mm of the effluent is continuously monitored. Fractions are collected and further analyzed by SDS-PAGE.

Fractions containing the Synferon polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the Synferon polypeptide (determined, for instance, by 16% SDS-PAGE) are then pooled.

The resultant Synferon polypeptide exhibits greater than 95% purity after the above refolding and purification steps. No major contaminant bands are observed from Commassie blue stained 16% SDS-PAGE gel when 5 μg of purified protein is loaded. The purified protein is also tested for endotoxin/LPS contamination, and typically the LPS content is less than 0.1 ng/ml according to LAL assays.

The following alternative method may be used to purify Synferon expressed in E coli when it is present in the form of inclusion bodies. Unless otherwise specified, all of the following steps are conducted at 4–10° C.

Upon completion of the production phase of the *E. coli* fermentation, the cell culture is cooled to 4–10° C. and the cells are harvested by continuous centrifugation at 15,000 rpm (Heraeus Sepatech). Oil the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells ware then lysed by passing the solution through a microfluidizer (Microfuidics, Corp. or APV Gaulin, Inc.) twice at 4000–6000 psi. The homogenate is then mixed with NaCl solution to a final concentration of 0.5 M NaCl, followed by centrifugation at 7000×g for 15 min. The resultant pellet is washed again using 0.5M NaCl, 100 mM Tris, 50 mM EDTA, pH 7.4.

The resulting washed inclusion bodies are solubilized with 1.5 M guanidine hydrochloride (GuHCl) for 2–4 hours. After 7000×g centrifugation for 15 min., the pellet is discarded and the Synferon polypeptide-containing supernatant is incubated at 4° C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mm NaCl, 2 mM EDTA by vigorous stirring. The refolded diluted protein solution is kept at 4° C. without mixing for 12 hours prior to further purification steps.

To clarify the refolded Synferon polypeptide solution, a previously prepared tangential filtration unit equipped with 0.16 μm membrane filter with appropriate surface area (e.g., Filtron), equilibrated with 40 mM sodium acetate, pH 6.0 is employed. The filtered sample is loaded onto a cation exchange resin (e.g., Poros HS-50, Perseptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 mm of the effluent is continuously monitored. Fractions are collected and further analyzed by SDS-PAGE.

Fractions containing the Synferon polypeptide are then pooled and mixed with 4 volumes of water. The diluted sample is then loaded onto a previously prepared set of tandem columns of strong anion (Poros HQ-50, Perseptive Biosystems) and weak anion (Poros CM-20, Perseptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant $A_{280}$ monitoring of the effluent. Fractions containing the Synferon polypeptide (determined, for instance, by 16% SDS-PAGE) are then pooled.

The resultant Synferon polypeptide exhibits greater than 95% purity after the above refolding and purification steps. No major contaminant bands are observed from Commassie blue stained 16% SDS-PAGE gel when 5 μg of purified protein is loaded. The purified protein is also tested for endotoxin/LPS contamination, and typically the LPS content is less than 0.1 ng/ml according to LAL assays.

Example 2

Cloning and Expression of Synferon protein in a Baculovirus Expression System

In this illustrative example, the plasmid shuttle vector pA2 GP is used to insert the cloned DNA encoding Synferon, into a baculovirus to express the Synferon protein, using a baculovirus leader and standard methods as described in Summers et al., A Manual of Methods for Baculovirus Vectors and Insect Cell Culture Procedures, Texas Agricultural Experimental Station Bulletin No. 1555 (1987). This expression vector contains the strong polyhedrin promoter of the *Autographa californica* nuclear polyhedrosis virus (AcMNPV) followed by the secretory signal peptide (leader) of the baculovirus gp67 protein and convenient restriction sites such as BamHI, Xba I and Asp718. The polyadenylation site of the simian virus 40 ("SV40") is used for efficient polyadenylation. For easy selection of recombinant virus, the plasmid contains the beta-galactosidase gene from *E. coli* under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate viable virus that expresses the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31–39 (19989).

The cDNA sequence encoding the mature Synferon protein in the deposited clone, lacking the AUG initiation codon and the naturally associated leader sequence shown in SEQ ID NO:2, is amplified using PCR oligonucleotide primers corresponding to the 5' and 3' sequences of the gene. The 5' primer has the sequence 5' CGCC GGATCCCTGCGACCTGCCGGAAACCCAC 3' (SEQ ID NO:6) containing the underlined BamHI restriction enzyme site. The 3' primer has the sequence 5' GCGCC GGTACCCTAAGCGATCAGACGAACCTGCAGGTTAG 3' (SEQ ID NO:7) containing the underlined Asp718 restriction site.

The amplified fragment is isolated from a 1% agarose gel using a commercially available kit ("Geneclean," BIO 101 Inc., La Jolla, Calif.). The fragment then is digested with BamHI and Asp718 and again is purified on a 1% agarose gel.

The plasmid is digested with the restriction enzymes BamHI and Asp718 and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

Fragment and the dephosphorylated plasmid are ligated together with T4 DNA ligase. *E. coli* HB101 or other suitable *E. coli* hosts such as XL-1 Blue (Statagene Cloning Systems, La Jolla, Calif.) cells are transformed with the ligation mixture and spread on culture plates. Bacteria are identified that contain the plasmid with the human Synferon gene by digesting DNA from individual colonies using BamHi and Asp718 and then analyzing the digestion product by gel electrophoresis. The sequence of the-cloned fragment is confirmed by DNA sequencing. This plasmid is designated herein pA2GPSynferon.

Five μg of the plasmid pA2GPSynferon is co-transfected with 1.0 μg of a commercially available linearized baculovirus DNA ("BaculoGold™ baculovirus DNA", Phanringen, San Diego, Calif.), using the lipofection method described by Felgner et al., *Proc. Natl. Acad. Sci. USA* 84: 7413–7417 (1987). One μg of BaculoGold™ virus DNA and 5 μg of the plasmid pA2GPSynferon are mixed in a sterile well of a microtiter plate containing 50 μl of serum-free Grace's medium (Life Technologies Inc., Gaithersburg, Md.). Afterwards, 10 μl Lipofectin plus 90 μl Grace's medium are added, mixed and incubated for 1 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added. Cultivation is then continued at 27° C. for four days.

After four days the supernanant is collected and a plaque assay is performed, as described by Summers and Smith, supra. An agarose gel with "Blue Gal" (Life Technologies Inc. now Invitrogen, Carlsbad, Calif.) is used to allow easy identification and isolation of gal-expression clones, which produce blue-stained plaques. (A detailed description of a "plaque assay" of this type can also be found in the user's guide for insect cell culture and baculovirology distributed by Life Technologies Inc., now Invitrogen, Carlsbad, Calif., page 9–10). After appropiate incubation, blue stained plaques are picked with the tip of a micropipettor (e.g., Eppendorf). The agar containing the recombinant viruses is then resuspended in a microcentrifuge tube containing 200 μl of Grace's medium and the suspension containing the recombinant baculovirus is used to infect Sf9 cells seeded in 35 mm dishes. Four days later the supernatants of these culture dishes are harvested and then they are stored at 4° C. The recombinant virus is called V-Synferon.

Five μg of the plasmid pA2GPSynferon is co-transfected with 1.0 μg of a commercially available linearized baculovirus DNA ("BaculoGold™ baculovirus DNA", Pharmingen, San Diego, Calif.), using the lipofection method described by Felgner et al., *Proc. Natl. Acad. Sci. USA* 84: 7413–7417 (1987). One μg of BaculoGold™ virus DNA and 5 μg of the plasmid pA2GPSynferon are mixed in a sterile well of a microtiter plate containing 50 μl of the serum-free Grace's medium (Life Technologies Inc., now Invetrogen, Carlsbad, Calif.). Afterwards, 10 μl Lipofectin plus 90 μl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27° C. The transfection solution is then removed from the plate and 1 ml of Grace's insect medium supplemented with 10% fetal calf serum is added. Cultivation is then continued at 27° C. for four days.

Microsequencing of the amino acid sequence of the amino terminus of purified protein may be used to determine the amino terminal sequence of the of the Synferon protein.

Example 3

Cloning and Expression of Synferon in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as pSVL and pMSG (Pharmacia, Uppsala, Sweden), pRSVcat (ATCC 37152), pSV2dhfr (ATCC 37146) and pBC12MI (ATCC 67109). Mammalian host cells that could be used include, human Hela, 293, H9 and Jurkat cells, mouse NIH3T3 and C127 cells, Cos 1, Cos 7 and CV1, quail QC1–3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, hygromycin allows the identification and isolation of the transfected cells.

The transfected gene can also be amplified to express large amounts of the encoded protein. The DHFR (dihydrofolate reductase) marker is useful to develop cell lines that carry several hundred or even several thousand copies of the gene of interest. Another useful selection marker is the enzyme glutamine synthase (GS) (Murphy et al., *Biochem J.* 227:277–279 (1991); Bebbington et al., *Bio/Technology* 10:169–175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen et al., *Molecular and Cellular Biology*, 438447 (March, 1985)) plus a fragment of the CMV-enhancer (Boshart et al., *Cell* 41:521–530 (1985)). Multiple cloning sites, e.g., with the restriction enzyme cleavage sites BamHI, XbaI and Asp718, facilitate the cloning of the gene of interest. The vectors contain in addition the 3' intron, the polyadenylation and termination signal of the rat preproinsulin gene.

Cloning and Expression in CHO Cells

The vector pC4-Sig is used for the expression of Synferon polypeptide. Plasmid pC4-Sig is a derivative of the plasmid pSV2-dhfr (ATCC Accession No. 37146). It contains coding region for the secretory leader sequence from chemokine beta-8 (see US95/09508) upstream from the multiple cloning site and is designed to be inframe with inserted heterologous DNA. The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies) supplemented with the chemotherapeutic agent methotrexate. The amplification of the DHFR genes in cells resistant to methotrexate (MTX) has been well documented (see, e.g., Alt, F. W., Kellems, R. M., Bertino, J. R., and Schimnke, R. T., 1978, *J. Biol. Chem.* 253:1357–1370, Hamlin, J. L. and Ma, C. 1990, *Biochem. et Biophys. Acta*, 1097: 107–143, Page, M. J. and Sydenham, M. A. 1991, *Biotechnology* 9:64–68). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rouse Sarcoma Virus (Cullen, et al., *Molecular and Cellular Biology*, March 1985:438–447) plus a fragment isolated from the enhancer of the immediate early gene of human cytomegalovirus (CMV) (Boshart et al., *Cell* 41:521–530 (1985)). Downstream of the promoter are the following single restriction enzyme cleavage sites that allow the integration of the genes: BamHI, Xba I, and Asp718. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the Synferon polypeptide in a regulated way in mammalian cells (Gossen, M., & Bujard, H. 1992, *Proc. Natl. Acad. Sci. USA* 89:5547–5551). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes BamHI and Asp718 and then dephosphorylated using calf intestinal phosphates by procedures known in the art. The vector is then isolated from a 1% agarose gel.

The DNA sequence encoding the Synferon polypeptide is amplified using PCR oligonucleotide primers corresponding to the 5' and 3' sequences of the desired portion of the gene. The 5' primer containing the underlined BamHI site, a Kozak sequence, and an AUG start codon, has the following sequence: 5' CGCC GGATCCTGCGACCTGCCGGAAACCCAC 3' (SEQ ID NO:8). The 3' primer, containing the underlined Asp718 restriction site has the following sequence: 5' GCGCC GGTACCCTAAGCGATCAGACGAACCTGCAGGTTAG 3' (SEQ ID NO:9).

The amplified fragment is digested with the endonucleases BamHI and Asp718 and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five µg of the expression plasmid pC4 is cotransfected with 0.5 µg of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of metothrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 µM, 2 µM, 5 µM, 10 mM, 20 mM). The same procedure is repeated until clones are obtained which grow at a concentration of 100–200 µM. Expression of the desired gene product is analyzed, for instance, by SDS-PAGE and Western blot or by reversed phase HPLC analysis.

It will be clear that the invention may be practiced otherwise than as particularly described in the foregoing description and examples. Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

In addition, the sequence listing attached hereto in both hard copy and computer readable form is hereby incorporated herein by reference.

What is claimed is:

1. An isolated antibody or fragment thereof that specifically binds to a protein selected from the group consisting of:
   (a) a protein consisting of amino acid residues 2 to 141 of SEQ ID NO:2;
   (b) a protein consisting of amino acid residues 1 to 139 of SEQ ID NO:2;
   (c) a protein consisting of amino acid residues 2 to 139 of SEQ ID NO:2;
   (d) a protein consisting of a portion of SEQ If) NO:2, wherein said portion consists of at least 30 contiguous amino acid residues of SEQ ID NO:2; and
   (e) a protein consisting of a portion of SEQ ID NO:2, wherein said portion consists of at least 50 contiguous amino acid residues of SEQ ID NO:2.

2. The antibody or fragment thereof of claim 1 that specifically binds protein (a).

3. The antibody or fragment thereof of claim 1 that specifically binds protein (b).

4. The antibody or fragment thereof of claim 1 that specifically binds protein (c).

5. The antibody or fragment thereof of claim 1 that specifically binds protein (d).

6. The antibody or fragment thereof of claim 1 that specifically binds protein (e).

7. The antibody or fragment thereof of claim 3 that specifically binds protein (a).

8. The antibody or fragment thereof of claim 3, wherein said protein bound by said antibody or fragment thereof is glycosylated.

9. The antibody or fragment thereof of claim 3 which is a polyclonal antibody.

10. The antibody or fragment thereof of claim 3 which is selected from the group consisting of:
    (a) a chimeric antibody; and
    (b) a Fab fragment.

11. The antibody or fragment thereof of claim 3 which is labeled.

12. The antibody of claim 11, wherein the label is selected from the group consisting of:
    (a) an enzyme;
    (b) a fluorescent label;
    (c) a luminescent label; and
    (d) a bioluminescent label.

13. The antibody or fragment thereof of claim 3, wherein said antibody specifically binds to said protein in a Western blot.

14. An isolated cell that produces the antibody or fragment thereof of claim 3.

15. A hybridoma that produces the antibody or fragment thereof of claim 3.

16. An isolated antibody or fragment thereof obtained from an animal that has been immunized with a protein selected from the group consisting of:
    (a) a protein comprising the amino acid sequence of amino acid residues 2 to 141 of SEQ ID NO:2;
    (b) a protein comprising the amino acid sequence of amino acid residues 1 to 139 of SEQ ID NO:2;
    (c) a protein comprising the amino acid sequence of amino acid residues 2 to 139 of SEQ ID NO:2;

39

(d) a protein consisting of an amino acid sequence of at least 30 contiguous amino acid residues of SEQ ID NO:2; and (e) a protein consisting of an amino acid sequence of at least 50 contiguous amino acid residues of SEQ ID NO:2;

wherein said antibody or fragment thereof specifically binds to said amino acid sequence.

17. The antibody or fragment thereof of claim 16 obtained from an animal immunized with protein (a).

18. The antibody or fragment thereof of claim 16 obtained from an animal immunized with protein (b).

19. The antibody or fragment thereof of claim 16 obtained from an animal immunized with protein (c).

20. The antibody or fragment thereof of claim 16 obtained from an animal immunized with protein (d).

21. The antibody or fragment thereof of claim 16 obtained from an animal immunized with protein (e).

22. The antibody or fragment thereof of claim 16 which is a monoclonal antibody.

23. The antibody or portion thereof of claim 16 which is selected from the group consisting of:

(a) a chimeric antibody;

(b) a polyclonal antibody; and (c) a Fab fragment.

24. An isolated monoclonal antibody or fragment thereof that specifically binds to a protein selected from the group consisting of:

(a) a protein consisting of amino acid residues 2 to 141 of SEQ ID NO:2;

(b) a protein consisting of amino acid residues 1 to 139 of SEQ ID NO:2;

(c) a protein consisting of amino acid residues 2 to 139 of SEQ ID NO:2;

(d) a protein consisting of a portion of SEQ ID NO:2, wherein said portion consists of at least 30 contiguous amino acid residues of SEQ ID NO:2; and (e) a protein consisting of a portion of SEQ ID NO:2, wherein said portion consists of at least 50 contiguous amino acid residues of SEQ ID NO:2.

25. The antibody or fragment thereof of claim 24 that specifically binds protein (a).

26. The antibody or fragment thereof of claim 24 that specifically binds protein (b).

27. The antibody or fragment thereof of claim 24 that specifically binds protein (c).

28. The antibody or fragment thereof of claim 24 that specifically binds protein (d).

29. The antibody or fragment thereof of claim 24 that specifically binds protein (e).

30. The antibody or fragment thereof of claim 26 that specifically binds protein (a).

31. The antibody or fragment thereof of claim 26, wherein said protein bound by said antibody or fragment thereof is glycosylated.

32. The antibody or fragment thereof of claim 26 which is selected from the group consisting of:

(a) a chimeric antibody; and (b) a Fab fragment.

33. The antibody or fragment thereof of claim 26 which is labeled.

34. The antibody of claim 33, wherein the label is selected from the group consisting of:

(a) an enzyme;

(b) a fluorescent label;

40

(c) a luminescent label; and (d) a bioluminescent label.

35. The antibody or fragment thereof of claim 26, wherein said antibody specifically binds to said protein in a Western blot.

36. An isolated cell that produces the antibody or fragment thereof of claim 26.

37. A hybridoma that produces the antibody or fragment thereof of claim 26.

38. An isolated antibody or fragment thereof that specifically binds to a protein selected from the group consisting of:

(a) a protein consisting of the full-length polypeptide encoded by the cDNA contained in ATCC Deposit Number 209522;

(b) a protein consisting of the full-length polypeptide minus the N-terminal methionine encoded by the cDNA contained in ATCC Deposit Number 209522;

(c) a protein consisting of a portion of the polypeptide encoded by the cDNA contained in ATCC Deposit Number 209522, where in said portion consists of at least 30 contiguous amino acid residues of the polypeptide encoded by the cDNA contained in ATCC Deposit Number 209522; and (d) a protein consisting of a portion of the polypeptide encoded by the cDNA contained in ATCC Deposit Number 209522, wherein said portion consists of at least 50 contiguous amino acid residues of the polypeptide encoded by the cDNA contained in ATCC Deposit Number 209522.

39. The antibody or fragment thereof of claim 38 that specifically binds protein (a).

40. The antibody or fragment thereof of claim 38 that specifically binds protein (b).

41. The antibody or fragment thereof of claim 38 that specifically binds protein (c).

42. The antibody or fragment thereof of claim 38 that specifically binds protein (d).

43. The antibody or fragment thereof of claim 39, wherein said protein bound by said antibody or fragment thereof is glycosylated.

44. The antibody or fragment thereof of claim 40 which is a polyclonal antibody.

45. The antibody or fragment thereof of claim 39 which is selected from the group consisting of:

(a) a chimeric antibody; and (b) a Fab fragment.

46. The antibody or fragment thereof of claim 39 which is labeled.

47. The antibody of claim 46, wherein the label is selected from the group consisting of:

(a) an enzyme;

(b) a fluorescent label;

(c) a luminescent label; and (d) a bioluminescent label.

48. The antibody or fragment thereof of claim 39, wherein said antibody specifically binds to said protein in a Western blot.

49. An isolated cell that produces the antibody or fragment thereof of claim 39.

50. A hybridoma that produces the antibody or fragment thereof of claim 39.

51. An isolated antibody or fragment thereof obtained from an animal that has been immunized with a protein selected from the group consisting of:

(a) a protein comprising the amino acid sequence of the full-length polypeptide encoded by the cDNA contained in ATCC Deposit Number 209522;

(b) a protein comprising the amino acid sequence of the full-length polypeptide minus the N-terminal methionine encoded by the cDNA contained in ATCC Deposit Number 209522;

(c) a protein consisting of an amino acid sequence of at least 30 contiguous amino acid residues of the polypeptide encoded by the cDNA contained in ATCC Deposit Number 209522; and (d) a protein consisting of an amino acid sequence of at least 50 contiguous amino acid residues the polypeptide encoded by the cDNA contained in ATCC Deposit Number 209522;

wherein said antibody or fragment thereof specifically binds to said amino acid sequence.

52. The antibody or fragment thereof of claim 51 obtained from an animal immunized with protein (a).

53. The antibody or fragment thereof of claim 51 obtained from an animal immunized with protein (b).

54. The antibody or fragment thereof of claim 51 obtained from an animal immunized with protein (c).

55. The antibody or fragment thereof of claim 51 obtained from an animal immunized with protein (d).

56. The antibody or fragment thereof of claim 51 which is a monoclonal antibody.

57. The antibody or portion thereof of claim 51 which is selected from the group consisting of:

(a) a chimeric antibody;

(b) a polyclonal antibody; and (c) a Fab fragment.

58. An isolated monoclonal antibody or fragment thereof that specifically binds to a protein selected from the group consisting of:

(a) a protein consisting of the full-length polypeptide encoded by the cDNA contained in ATCC Deposit Number 209522;

(b) a protein consisting of the full-length polypeptide minus the N-terminal methionine encoded by the cDNA contained in ATCC Deposit Number 209522;

(c) a protein consisting of a portion of the polypeptide encoded by the cDNA contained in ATCC Deposit Number 20953, wherein said portion consists of at least 30 contiguous amino acid residues of the polypeptide encoded by the cDNA contained in ATCC Deposit Number 209522; and (d) a protein consisting of a portion of the polypeptide encoded by the cDNA contained in ATCC Deposit Number 20953, wherein said portion consists of at least 50 contiguous amino acid residues of the polypeptide encoded by the cDNA contained in ATCC Deposit Number 209522.

59. The antibody or fragment thereof of claim 58 that specifically binds protein (a).

60. The antibody or fragment thereof of claim 58 that specifically binds protein (b).

61. The antibody or fragment thereof of claim 58 that specifically binds protein (c).

62. The antibody or fragment thereof of claim 58 that specifically binds protein (d).

63. The antibody or fragment thereof of claim 59, wherein said protein bound by said antibody or fragment thereof is glycosylated.

64. The antibody or fragment thereof of claim 59 which is selected from the group consisting of:

(a) a chimeric antibody; and (b) a Fab fragment.

65. The antibody or fragment thereof of claim 59 which is labeled.

66. The antibody of claim 65, wherein the label is selected from the group consisting of:

(a) an enzyme;

(b) a fluorescent label;

(c) a luminescent label; and (d) a bioluminescent label.

67. The antibody or fragment thereof of claim 59, wherein said antibody specifically binds to said protein in a Western blot.

68. An isolated cell that produces the antibody or fragment thereof of claim 59.

69. A hybridoma that produces the antibody or fragment thereof of claim 59.

* * * * *

UNITED STATES PATENT AND TRADEMARK OFFICE
CERTIFICATE OF CORRECTION

PATENT NO. : 6,548,063 B1
DATED : April 15, 2003
INVENTOR(S) : Olsen et al.

It is certified that error appears in the above-identified patent and that said Letters Patent is hereby corrected as shown below:

Column 37,
Line 38, claim 1, should read:

1. An isolated antibody or fragment thereof that specifically binds to a protein selected from the group consisting of:
   (a) a protein consisting of amino acid residues 2 to 141 of SEQ ID NO:2;
   (b) a protein consisting of amino acid residues 1 to 161 of SEQ ID NO:2;
   (c) a protein consisting of amino acid residues 2 to 161 of SEQ ID NO:2;
   (d) a protein consisting of a portion of SEQ ID NO:2, wherein said portion consists of at least 30 contiguous amino acid residues of SEQ ID NO:2; and
   (e) a protein consisting of a portion of SEQ ID NO:2, wherein said portion consists of at least 50 contiguous amino acid residues of SEQ ID NO:2.

Column 38,
Line 58, claim 16, should read:

16. An isolated antibody or fragment thereof obtained from an animal that has been immunized with a protein selected from the group consisting of:
   (a) a protein comprising the amino acid sequence of amino acid residues 2 to 141 of SEQ ID NO:2;
   (b) a protein comprising the amino acid sequence of amino acid residues 1 to 161 of SEQ ID NO:2;
   (c) a protein comprising the amino acid sequence of amino acid residues 2 to 161 of SEQ ID NO:2;
   (d) a protein consisting of an amino acid sequence of at least 30 contiguous amino acid residues of SEQ ID NO:2; and
   (e) a protein consisting of an amino acid sequence of at least 50 contiguous amino acid residues of SEQ ID NO:2;
   wherein said antibody or fragment thereof specifically binds to said amino acid sequence.

Column 39,
Line 26, claim 24, should read:

24. An isolated monoclonal antibody or fragment thereof that specifically binds to a protein selected from the group consisting of:
   (a) a protein consisting of amino acid residues 2 to 141 of SEQ ID NO:2;
   (b) a protein consisting of amino acid residues 1 to 161 of SEQ ID NO:2;
   (c) a protein consisting of amino acid residues 2 to 161 of SEQ ID NO:2;
   (d) a protein consisting of a portion of SEQ ID NO:2, wherein said portion consists of at least 30 contiguous amino acid residues of SEQ ID NO:2; and
   (e) a protein consisting of a portion of SEQ ID NO:2, wherein said portion consists of at least 50 contiguous amino acid residues of SEQ ID NO:2.

UNITED STATES PATENT AND TRADEMARK OFFICE
CERTIFICATE OF CORRECTION

PATENT NO. : 6,548,063 B1
DATED : April 15, 2003
INVENTOR(S) : Olsen et al.

It is certified that error appears in the above-identified patent and that said Letters Patent is hereby corrected as shown below:

<u>Column 41,</u>
Line 34, claim 58, should read:

58. An isolated monoclonal antibody or fragment thereof that specifically binds to a protein selected from the group consisting of:
    (a) a protein consisting of the full-length polypeptide encoded by the cDNA contained in ATCC Deposit Number 209522;
    (b) a protein consisting of the full-length polypeptide minus the N-terminal methionine encoded by the cDNA contained in ATCC Deposit Number 209522;
    (c) a protein consisting of a portion of the polypeptide encoded by the cDNA contained in ATCC Deposit Number 209522, wherein said portion consists of at least 30 contiguous amino acid residues of the polypeptide encoded by the cDNA contained in ATCC Deposit Number 209522; and
    (d) a protein consisting of a portion of the polypeptide encoded by the cDNA contained in ATCC Deposit Number 209522, wherein said portion consists of at least 50 contiguous amino acid residues of the polypeptide encoded by the cDNA contained in ATCC Deposit Number 209522.

Signed and Sealed this

Twenty-fourth Day of August, 2004

JON W. DUDAS
*Director of the United States Patent and Trademark Office*

SEQUENCE LISTING

<160> NUMBER OF SEQ ID NOS: 9

<210> SEQ ID NO 1
<211> LENGTH: 483
<212> TYPE: DNA
<213> ORGANISM: Homo sapiens
<220> FEATURE:
<221> NAME/KEY: CDS
<222> LOCATION: (1)..(483)

<400> SEQUENCE: 1

| atg | tgc | gac | ctg | ccg | gaa | acc | cac | tct | ctg | gac | tct | cgt | aac | acc | acc | 48 |
|---|---|---|---|---|---|---|---|---|---|---|---|---|---|---|---|---|
| Met | Cys | Asp | Leu | Pro | Glu | Thr | His | Ser | Leu | Asp | Ser | Arg | Asn | Thr | Thr | |
| 1 | | | | 5 | | | | | 10 | | | | | 15 | | |

| gtt | ctg | ctg | cac | cag | atg | cgt | cgt | atc | tct | ccg | tct | ctg | tgc | ctg | aaa | 96 |
|---|---|---|---|---|---|---|---|---|---|---|---|---|---|---|---|---|
| Val | Leu | Leu | His | Gln | Met | Arg | Arg | Ile | Ser | Pro | Ser | Leu | Cys | Leu | Lys | |
| | | | 20 | | | | | 25 | | | | | 30 | | | |

| gac | cgt | cac | gac | ttc | ggt | ttc | ccg | cag | gaa | gaa | gtt | aaa | ggt | tct | aaa | 144 |
|---|---|---|---|---|---|---|---|---|---|---|---|---|---|---|---|---|
| Asp | Arg | His | Asp | Phe | Gly | Phe | Pro | Gln | Glu | Glu | Val | Lys | Gly | Ser | Lys | |
| | | 35 | | | | | 40 | | | | | 45 | | | | |

| atc | cag | aaa | gct | cac | acc | acc | gtt | ctg | cac | aaa | gtt | ctg | cag | cag | 192 |
|---|---|---|---|---|---|---|---|---|---|---|---|---|---|---|---|
| Ile | Gln | Lys | Ala | His | Thr | Thr | Thr | Val | Leu | His | Lys | Val | Leu | Gln | Gln | |
| 50 | | | | | 55 | | | | | 60 | | | | | | |

| atc | gtt | acc | ctg | ttc | aac | acc | cgt | tct | gtt | ggt | tgg | aac | gaa | acc | ggt | 240 |
|---|---|---|---|---|---|---|---|---|---|---|---|---|---|---|---|---|
| Ile | Val | Thr | Leu | Phe | Asn | Thr | Arg | Ser | Val | Gly | Trp | Asn | Glu | Thr | Gly | |
| 65 | | | | 70 | | | | | 75 | | | | | 80 | | |

| ctg | gaa | aaa | ctg | ttc | acc | gaa | ttc | tac | cag | cac | tgg | gaa | gtt | ctg | gaa | 288 |
|---|---|---|---|---|---|---|---|---|---|---|---|---|---|---|---|---|
| Leu | Glu | Lys | Leu | Phe | Thr | Glu | Phe | Tyr | Gln | His | Trp | Glu | Val | Leu | Glu | |
| | | | 85 | | | | | 90 | | | | | 95 | | | |

| ccg | tgc | ctg | ctg | aac | gaa | ctg | ggt | gtt | gaa | ggt | ctg | tct | cag | gct | atg | 336 |
|---|---|---|---|---|---|---|---|---|---|---|---|---|---|---|---|---|
| Pro | Cys | Leu | Leu | Asn | Glu | Leu | Gly | Val | Glu | Gly | Leu | Ser | Gln | Ala | Met | |
| | | 100 | | | | | 105 | | | | | 110 | | | | |

| acc | acc | ccg | aac | gct | gtt | aaa | tct | tac | ttc | cag | ggt | atc | tct | ctg | tac | 384 |
|---|---|---|---|---|---|---|---|---|---|---|---|---|---|---|---|---|
| Thr | Thr | Pro | Asn | Ala | Val | Lys | Ser | Tyr | Phe | Gln | Gly | Ile | Ser | Leu | Tyr | |
| | | 115 | | | | | 120 | | | | | 125 | | | | |

| ctg | gaa | aaa | aaa | gaa | gaa | tct | ctg | tgc | acc | tgg | gaa | gtt | ggt | gct | gaa | 432 |
|---|---|---|---|---|---|---|---|---|---|---|---|---|---|---|---|---|
| Leu | Glu | Lys | Lys | Glu | Glu | Ser | Leu | Cys | Thr | Trp | Glu | Val | Gly | Ala | Glu | |
| | 130 | | | | | 135 | | | | | 140 | | | | | |

| atc | atg | cgt | tct | ttc | ttc | ttc | tct | tct | aac | ctg | cag | gtt | cgt | ctg | atc | 480 |
|---|---|---|---|---|---|---|---|---|---|---|---|---|---|---|---|---|
| Ile | Met | Arg | Ser | Phe | Phe | Phe | Ser | Ser | Asn | Leu | Gln | Val | Arg | Leu | Ile | |
| 145 | | | | 150 | | | | | 155 | | | | | 160 | | |

| gct | 483 |
|---|---|
| Ala | |

<210> SEQ ID NO 2
<211> LENGTH: 161
<212> TYPE: PRT
<213> ORGANISM: Homo sapiens

<400> SEQUENCE: 2

Met Cys Asp Leu Pro Glu Thr His Ser Leu Asp Ser Arg Asn Thr Thr
1               5                   10                  15

Val Leu Leu His Gln Met Arg Arg Ile Ser Pro Ser Leu Cys Leu Lys
            20                  25                  30

Asp Arg His Asp Phe Gly Phe Pro Gln Glu Glu Val Lys Gly Ser Lys
        35                  40                  45

Ile Gln Lys Ala His Thr Thr Thr Val Leu His Lys Val Leu Gln Gln
    50                  55                  60

Ile Val Thr Leu Phe Asn Thr Arg Ser Val Gly Trp Asn Glu Thr Gly

```
                65                  70                  75                  80
Leu Glu Lys Leu Phe Thr Glu Phe Tyr Gln His Trp Glu Val Leu Glu
                    85                  90                  95
Pro Cys Leu Leu Asn Glu Leu Gly Val Glu Gly Leu Ser Gln Ala Met
                100                 105                 110
Thr Thr Pro Asn Ala Val Lys Ser Tyr Phe Gln Gly Ile Ser Leu Tyr
                115                 120                 125
Leu Glu Lys Lys Glu Glu Ser Leu Cys Thr Trp Glu Val Gly Ala Glu
            130                 135                 140
Ile Met Arg Ser Phe Phe Ser Ser Asn Leu Gln Val Arg Leu Ile
145                 150                 155                 160
Ala

<210> SEQ ID NO 3
<211> LENGTH: 162
<212> TYPE: PRT
<213> ORGANISM: Homo sapiens

<400> SEQUENCE: 3

Cys Asp Leu Pro Gln Asn His Gly Leu Leu Ser Arg Asn Thr Leu Val
1               5                   10                  15
Leu Leu His Gln Met Arg Arg Ile Ser Pro Phe Leu Cys Leu Lys Asp
                20                  25                  30
Arg Arg Asp Phe Arg Phe Pro Gln Glu Met Val Lys Gly Ser Gln Leu
            35                  40                  45
Gln Lys Ala His Val Met Ser Val Leu His Glu Met Leu Gln Gln Ile
        50                  55                  60
Phe Ser Leu Phe His Thr Glu Arg Ser Ser Ala Ala Trp Asn Met Thr
65                  70                  75                  80
Leu Leu Asp Gln Leu His Thr Gly Leu His Gln Gln Leu Gln His Leu
                85                  90                  95
Glu Thr Cys Leu Leu Gln Val Val Gly Glu Gly Glu Ser Ala Gly Ala
                100                 105                 110
Ile Ser Ser Pro Ala Leu Thr Leu Arg Arg Tyr Phe Gln Gly Ile Arg
            115                 120                 125
Val Tyr Leu Lys Glu Lys Lys Tyr Ser Asp Cys Ala Trp Glu Val Val
        130                 135                 140
Arg Met Glu Ile Met Lys Ser Leu Phe Leu Ser Thr Asn Met Gln Glu
145                 150                 155                 160
Arg Leu

<210> SEQ ID NO 4
<211> LENGTH: 34
<212> TYPE: DNA
<213> ORGANISM: Homo sapiens

<400> SEQUENCE: 4
gggaattcca tatgtgcgac ctgccggaaa ccca                              34

<210> SEQ ID NO 5
<211> LENGTH: 40
<212> TYPE: DNA
<213> ORGANISM: Homo sapiens

<400> SEQUENCE: 5
gcgccggtac cctaagcgat cagacgaacc tgcaggttag                        40
```

```
<210> SEQ ID NO 6
<211> LENGTH: 32
<212> TYPE: DNA
<213> ORGANISM: Homo sapiens

<400> SEQUENCE: 6
cgccggatcc ctgcgacctg ccggaaaccc ac                                    32

<210> SEQ ID NO 7
<211> LENGTH: 40
<212> TYPE: DNA
<213> ORGANISM: Homo sapiens

<400> SEQUENCE: 7
gcgccggtac cctaagcgat cagacgaacc tgcaggttag                            40

<210> SEQ ID NO 8
<211> LENGTH: 31
<212> TYPE: DNA
<213> ORGANISM: Homo sapiens

<400> SEQUENCE: 8
cgccggatcc tgcgacctgc cggaaaccca c                                     31

<210> SEQ ID NO 9
<211> LENGTH: 40
<212> TYPE: DNA
<213> ORGANISM: Homo sapiens

<400> SEQUENCE: 9
gcgccggtac cctaagcgat cagacgaacc tgcaggttag                            40
```